United States Patent [19]

Ohsaki et al.

[11] Patent Number: 5,428,129

[45] Date of Patent: Jun. 27, 1995

[54] PEPTIDES AND PROCESSES FOR PRODUCING CYCLIC PEPTIDES

[75] Inventors: Masutaka Ohsaki; Satoshi Kishida; Takashi Inoue, all of Tsuchiura, Japan

[73] Assignee: Daicel Chemical Industries, Osaka, Japan

[21] Appl. No.: 726,843

[22] Filed: Jul. 8, 1991

Related U.S. Application Data

[63] Continuation of PCT/JP90/01440 filed Nov. 7, 1990.

[30] Foreign Application Priority Data

Nov. 8, 1989 [JP] Japan ................. 1-290660

[51] Int. Cl.$^6$ ............... C07K 1/02; C07K 1/04; C07K 14/585
[52] U.S. Cl. .................... 530/307; 530/332; 530/334; 530/338; 530/339; 930/60; 930/DIG. 537
[58] Field of Search ............ 514/9, 11; 930/537, 930/538, 539, 541, 60; 530/332, 307, 333, 334, 338, 339

[56] References Cited

U.S. PATENT DOCUMENTS

| | | | |
|---|---|---|---|
| 4,043,992 | 8/1977 | Fujimoto et al. | 530/345 |
| 4,086,221 | 4/1978 | Sakakibara et al. | 530/307 |
| 4,146,612 | 3/1979 | Veber | 514/11 |
| 4,161,521 | 7/1979 | Veber et al. | 514/11 |
| 4,277,393 | 7/1981 | Sakakibara et al. | 530/307 |
| 4,658,014 | 4/1987 | Kempe | 530/307 |
| 4,743,677 | 5/1988 | Noda et al. | 530/307 |

FOREIGN PATENT DOCUMENTS

| | | |
|---|---|---|
| 91909390 | 3/1983 | European Pat. Off. |
| 2592049 | 6/1987 | France |
| 2-219589 | 9/1990 | Japan |
| 1590645 | 6/1981 | United Kingdom |
| 87/03884 | 7/1987 | WIPO |

OTHER PUBLICATIONS

Chemical Abstracts vol. 109:129696e (1988).
Chemical Abstracts vol. 114:99992g (1991).
"Nonreducible Cyclic Analogues of Somatostatin", *Journal of The American Chemical Society*, 98:8, Apr. 14, 1976 pp. 2367–2369.

*Primary Examiner*—Jeffrey E. Russel
*Attorney, Agent, or Firm*—Spencer, Frank & Schneider

[57] ABSTRACT

In this invention, a peptide of the following general formula is subjected to cyclization reaction to produce a cyclic peptide, preferably a synthetic calcitonin derivative (elcatonin) which is a useful medicine.

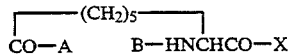

(wherein A and B form a peptide of the formula Ser-Asn-Leu-Ser-Thr (SEQ ID NO: 47); X means a hydroxyl group, a carboxy-protecting group, an amino acid residue or a peptide residue; provided that the side-chain carboxyl group of α-L-aminosuberic acid is condensed with an amino acid or a peptide).

The cyclic peptide can be obtained by subjecting a peptide of the above general formula to (1) cyclization reaction by chemical condensation, (2) cyclization reaction in the presence of an alkali metal salt and (3) reactions using the techniques of liquid phase synthesis and solid phase synthesis in combination.

14 Claims, No Drawings

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Cross-links
        ( B ) LOCATION: join(1..6)
        ( D ) OTHER INFORMATION: /note="L-aminosuberic acid forms a linkage between positions 1 and 6"

( i x ) FEATURE:
    ( A ) NAME/KEY: Modified-site
    ( B ) LOCATION: 31
    ( D ) OTHER INFORMATION: /note=carboxylamide ( x i ) SEQUENCE DESCRIPTION: SEQ ID NO:1:

```
Ser Asn Leu Ser Thr Xaa Val Leu Gly Lys Leu Ser Gln Glu Leu His
1               5                   10                  15

Lys Leu Gln Thr Tyr Pro Arg Thr Asp Val Gly Ala Gly Thr Pro
            20              25                  30
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 6
        ( D ) OTHER INFORMATION: /note="L-aminosuberic acid;
            carboxyl group may have a hydroxyl group, a
            carboxy- protecting group, an amino acid residue
            or a peptide residue"

( x i ) SEQUENCE DESCRIPTION: SEQ ID NO:2:

```
Ser Asn Leu Ser Thr Xaa
1               5
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: NO ( i v ) ANTI-SENSE: NO ( i x ) FEATURE:
        ( A ) NAME/KEY: Cross-links
        ( B ) LOCATION: join(1..6)
        ( D ) OTHER INFORMATION: /note="L-aminosuberic acid forms a
            linkage between pos 1 and 6; carboxyl group may
            have a hydroxyl group, a carboxy-protecting group,
            an amino acid residue, or a peptide residue."

( x i ) SEQUENCE DESCRIPTION: SEQ ID NO:3:

```
Ser Asn Leu Ser Thr Xaa
1               5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular ( i i ) MOLECULE TYPE: peptide ( i i i ) HYPOTHETICAL: NO ( i x ) FEATURE:
    ( A ) NAME/KEY: Cross-links
    ( B ) LOCATION: join(1..6)
    ( D ) OTHER INFORMATION: /note="L-aminosuberic acid forms a
        linkage between pos 1 and 6; carboxyl group may
        have a hydroxyl group or a peptide residue of
        formula VII in spec"

( x i ) SEQUENCE DESCRIPTION: SEQ ID NO:4:

Ser Asn Leu Ser Thr Xaa
1               5

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 25
        ( D ) OTHER INFORMATION: /note="amidated"

( x i ) SEQUENCE DESCRIPTION: SEQ ID NO:5:

Val Leu Gly Lys Leu Ser Gln Glu Leu His Lys Leu Gln Thr Tyr Pro
1               5                   10                  15

Arg Thr Asp Val Gly Ala Gly Thr Pro
            20                  25

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /note="L-aminosuberic acid;
        carboxyl group of L-aminosuberic acid has a
        carboxy- protecting group"

( i x ) FEATURE:
        ( A ) NAME/KEY: Modified-site
        ( B ) LOCATION: 2, 5 and 6
        ( D ) OTHER INFORMATION: /note="benzyl at Ser (pos 2), Ser
        ( p o s 5 ) and Thr (pos 6)"

( x i ) SEQUENCE DESCRIPTION: SEQ ID NO:6:

Xaa Ser Asn Leu Ser Thr
1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: circular (i i) MOLECULE TYPE: peptide (i i i) HYPOTHETICAL: NO (i v) ANTI-SENSE: NO (i x) FEATURE:
 (A) NAME/KEY: Modified-site
 (B) LOCATION: 3
 (D) OTHER INFORMATION: /note="L-aminosuberic acid;
  carboxyl group of L-aminosuberic acid has a
  carboxy- protecting group"

(x i) SEQUENCE DESCRIPTION: SEQ ID NO:7:

```
Ser  Thr  Xaa  Ser  Asn  Leu
1                 5
```

(2) INFORMATION FOR SEQ ID NO:8:

(i) SEQUENCE CHARACTERISTICS:
  (A) LENGTH: 22 amino acids
  (B) TYPE: amino acid
  (C) STRANDEDNESS: single
  (D) TOPOLOGY: linear (i i) MOLECULE TYPE: peptide (i i i) HYPOTHETICAL: NO (i v) ANTI-SENSE: NO (i x) FEATURE:
  (A) NAME/KEY: Modified-site
  (B) LOCATION: 1
  (D) OTHER INFORMATION: /note="either Val-Leu-Gly"in
   an amide linkage or hydrogen"

(x i) SEQUENCE DESCRIPTION: SEQ ID NO:8:

```
Lys  Leu  Ser  Gln  Glu  Leu  His  Lys  Leu  Gln  Thr  Tyr  Pro  Arg  Thr  Asp
1                 5                        10                       15

Val  Gly  Ala  Gly  Thr  Pro
              20
```

(2) INFORMATION FOR SEQ ID NO:9:

(i) SEQUENCE CHARACTERISTICS:
  (A) LENGTH: 6 amino acids
  (B) TYPE: amino acid
  (C) STRANDEDNESS: single
  (D) TOPOLOGY: circular (i i) MOLECULE TYPE: peptide (i i i) HYPOTHETICAL: NO (i v) ANTI-SENSE: NO (v) FRAGMENT TYPE: internal (i x) FEATURE:
  (A) NAME/KEY: Cross-links
  (B) LOCATION: join(1..6)
  (D) OTHER INFORMATION: /note="L-aminosuberic ester forms
   a linkage between positions 1 and 6"

(i x) FEATURE:
  (A) NAME/KEY: Modified-site
  (B) LOCATION: 1, 4 and 5
  (D) OTHER INFORMATION: /note="benzyl at Ser (pos 1), Ser
   (pos 4) and Thr (pos 5)"

(x i) SEQUENCE DESCRIPTION: SEQ ID NO:9:

```
Ser  Asn  Leu  Ser  Thr  Xaa
1                 5
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4
        (D) OTHER INFORMATION: /note="L-aminosuberic ester at pos 4"

(ix) FEATURE:
        (A) NAME/KEY: Modified-site
        (B) LOCATION: 2, 3 and 5
        (D) OTHER INFORMATION: /note="benzyl at Ser (pos 2), Thr (pos 3) and Ser (pos 5)"

(xi) SEQUENCE DESCRIPTION: SEQ ID NO:10:

Leu Ser Thr Xaa Ser Asn
1                5

(2) INFORMATION FOR SEQ ID NO:11:

(i) SEQUENCE CHARACTERISTICS:
        (A) LENGTH: 31 amino acids
        (B) TYPE: amino acid
        (C) STRANDEDNESS: single
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Cross-links
        (B) LOCATION: join(1..6)
        (D) OTHER INFORMATION: /note="L-aminosuberic acid forms a linkage between positions 1 and 6"

(ix) FEATURE:
        (A) NAME/KEY: Modified-site
        (B) LOCATION: 1, 4, 5, 12, 20, 24 and 30)
        (D) OTHER INFORMATION: /note="benzyl"

(ix) FEATURE:
        (A) NAME/KEY: Modified-site
        (B) LOCATION: 14 and 25
        (D) OTHER INFORMATION: /note="benzyl ester"

(ix) FEATURE:
        (A) NAME/KEY: Modified-site
        (B) LOCATION: 16 and 23
        (D) OTHER INFORMATION: /note="tosyl"

(ix) FEATURE:
        (A) NAME/KEY: Modified-site
        (B) LOCATION: 21
        (D) OTHER INFORMATION: /note="2-bromobenzyloxycarboxyl"

(ix) FEATURE:
        (A) NAME/KEY: Modified-site
        (B) LOCATION: 10 and 17
        (D) OTHER INFORMATION: /note="2-chlorobenzyloxycarboxyl"

(xi) SEQUENCE DESCRIPTION: SEQ ID NO:11:

Ser Asn Leu Ser Thr Xaa Val Leu Gly Lys Leu Ser Gln Glu Leu His
1            5                    10                  15

Lys Leu Gln Thr Tyr Pro Arg Thr Asp Val Gly Ala Gly Thr Pro
            20                  25                      30

( 2 ) INFORMATION FOR SEQ ID NO:12:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 3, 11, 15 and 21
        ( D ) OTHER INFORMATION: /note="benzyl"

( i x ) FEATURE:
        ( A ) NAME/KEY: Modified-site
        ( B ) LOCATION: 5 and 16
        ( D ) OTHER INFORMATION: /note="benzyl ester"

( i x ) FEATURE:
        ( A ) NAME/KEY: Modified-site
        ( B ) LOCATION: 7 and 14
        ( D ) OTHER INFORMATION: /note="tosyl"

( i x ) FEATURE:
        ( A ) NAME/KEY: Modified-site
        ( B ) LOCATION: 12
        ( D ) OTHER INFORMATION: /note="2-bromobenzyloxycarbonyl"

( i x ) FEATURE:
        ( A ) NAME/KEY: Modified-site
        ( B ) LOCATION: 1 and 8
        ( D ) OTHER INFORMATION: /note="2-chlorobenzyloxycarbonyl"

( i x ) FEATURE:
        ( A ) NAME/KEY: Modified-site
        ( B ) LOCATION: 1
        ( D ) OTHER INFORMATION: /note="tert-butoxycarbonyl or H"

( x i ) SEQUENCE DESCRIPTION: SEQ ID NO:12:

Lys Leu Ser Gln Glu Leu His Lys Leu Gln Thr Tyr Pro Arg Thr Asp
1                   5                       10                      15

Val Gly Ala Gly Thr Pro
                20

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Cross-links
        ( B ) LOCATION: join(1..6)
        ( D ) OTHER INFORMATION: /note="L-aminosuberic acid forms a
            linkage between positions 1 and 6"

( i x ) FEATURE:
        ( A ) NAME/KEY: Modified-site
        ( B ) LOCATION: 1, 4 and 5
        ( D ) OTHER INFORMATION: /note="benzyl"

( x i ) SEQUENCE DESCRIPTION: SEQ ID NO:13:

Ser Asn Leu Ser Thr Xaa Val Leu Gly
1               5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 3
        ( D ) OTHER INFORMATION: /note="L-aminosuberic ester"

( i x ) FEATURE:
        ( A ) NAME/KEY: Modified-site
        ( B ) LOCATION 1
        ( D ) OTHER INFORMATION: /note="tert-butoxycarbonyl"

( i x ) FEATURE:
        ( A ) NAME/KEY: Modified-site
        ( B ) LOCATION: 1, 2 and 4
        ( D ) OTHER INFORMATION: /note="benzyl"

( x i ) SEQUENCE DESCRIPTION: SEQ ID NO:14:

Ser Thr Xaa Ser Asn
1               5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 4
        ( D ) OTHER INFORMATION: /note="L-aminosuberic ester"

( i x ) FEATURE:
        ( A ) NAME/KEY: Modified-site
        ( B ) LOCATION: 1
        ( D ) OTHER INFORMATION: /note="tert-butoxycarbonyl"

( i x ) FEATURE:
        ( A ) NAME/KEY: Modified-site
        ( B ) LOCATION: 2, 3 and 5)
        ( D ) OTHER INFORMATION: /note="benzyl"

( x i ) SEQUENCE DESCRIPTION: SEQ ID NO:15:

Leu Ser Thr Xaa Ser Asn
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid (C) STRANDEDNESS: single
(D) TOPOLOGY: circular (ii) MOLECULE TYPE: peptide (iii) HYPOTHETICAL: NO (iv) ANTI-SENSE: NO (ix) FEATURE:
    (A) NAME/KEY: Cross-links
    (B) LOCATION: join(1..6)
    (D) OTHER INFORMATION: /note="L-aminosuberic acid forms a linkage between positions 1 and 6"

(ix) FEATURE:
    (A) NAME/KEY: Modified-site
    (B) LOCATION: 1, 4 and 5
    (D) OTHER INFORMATION: /note="benzyl"

(xi) SEQUENCE DESCRIPTION: SEQ ID NO:16:

Ser Asn Leu Ser Thr Xaa
1               5

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single
        (D) TOPOLOGY: both (ii) MOLECULE TYPE: peptide (iii) HYPOTHETICAL: NO (iv) ANTI-SENSE: NO (ix) FEATURE:
        (A) NAME/KEY: Cross-links
        (B) LOCATION: join(1..6)
        (D) OTHER INFORMATION: /note="L-aminosuberic acid forms a linkage between positions 1 and 6"

(ix) FEATURE:
        (A) NAME/KEY: Modified-site
        (B) LOCATION: 1, 4 and 5
        (D) OTHER INFORMATION: /note="benzyl"

(ix) FEATURE:
        (A) NAME/KEY: Modified-site
        (B) LOCATION: 9
        (D) OTHER INFORMATION: /note="phenacyl ester"

(xi) SEQUENCE DESCRIPTION: SEQ ID NO:17:

Ser Asn Leu Ser Thr Xaa Val Leu Gly
1               5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 5
        (D) OTHER INFORMATION: /note="L-aminosuberic ester"

(ix) FEATURE:

(A) NAME/KEY: Modified-site
(B) LOCATION: 3, 4 and 6
(D) OTHER INFORMATION: /note="benzyl"

(x i) SEQUENCE DESCRIPTION: SEQ ID NO:18:

Asn Leu Ser Thr Xaa Ser
1               5

(2) INFORMATION FOR SEQ ID NO:19:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (i x) FEATURE:
(A) NAME/KEY: Modified-site
(B) LOCATION: 1
(D) OTHER INFORMATION: /note="tert-butoxycarbonyl"

(i x) FEATURE:
(A) NAME/KEY: Modified-site
(B) LOCATION: 3, 4 and 6
(D) OTHER INFORMATION: /note="benzyl"

(i x) FEATURE:
(A) NAME/KEY: Modified-site
(B) LOCATION: 5
(D) OTHER INFORMATION: /note="L-aminosuberic ester"

(x i) SEQUENCE DESCRIPTION: SEQ ID NO:19:

Asn Leu Ser Thr Xaa Ser
1               5

(2) INFORMATION FOR SEQ ID NO:20:

(i) SEQUENCE CHARACTERISTICS:
(A) LENGTH: 5 amino acids
(B) TYPE: amino acid
(C) STRANDEDNESS: single
(D) TOPOLOGY: linear (i i) MOLECULE TYPE: peptide (i i i) HYPOTHETICAL: NO (i v) ANTI-SENSE: NO (i x) FEATURE:
(A) NAME/KEY: Modified-site
(B) LOCATION: 4
(D) OTHER INFORMATION: /note="L-aminosuberic ester"

(i x) FEATURE:
(A) NAME/KEY: Modified-site
(B) LOCATION: 1
(D) OTHER INFORMATION: /note="tert-butoxycarbonyl"

(i x) FEATURE:
(A) NAME/KEY: Modified-site
(B) LOCATION: 2, 3 and 5)
(D) OTHER INFORMATION: /note="benzyl"

(i x) FEATURE:
(A) NAME/KEY: Modified-site
(B) LOCATION: 5
(D) OTHER INFORMATION: /note="phenacyl ester"

(x i) SEQUENCE DESCRIPTION: SEQ ID NO:20:

Leu Ser Thr Xaa Ser (2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 5
        (D) OTHER INFORMATION: /note="L-aminosuberic ester"

(ix) FEATURE:
        (A) NAME/KEY: Modified-site
        (B) LOCATION: 1
        (D) OTHER INFORMATION: /note="tert-butoxycarbonyl"

(ix) FEATURE:
        (A) NAME/KEY: Modified-site
        (B) LOCATION: 3, 4 and 6
        (D) OTHER INFORMATION: /note="benzyl"

(ix) FEATURE:
        (A) NAME/KEY: Modified-site
        (B) LOCATION: 6
        (D) OTHER INFORMATION: /note="phenacyl ester"

(xi) SEQUENCE DESCRIPTION: SEQ ID NO:21:

Asn Leu Ser Thr Xaa Ser
1               5

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 3
        (D) OTHER INFORMATION: /note="L-aminosuberic ester"

(ix) FEATURE:
        (A) NAME/KEY: Modified-site
        (B) LOCATION: 1, 2 and 4
        (D) OTHER INFORMATION: /note="benzyl"

(xi) SEQUENCE DESCRIPTION: SEQ ID NO:22:

Ser Thr Xaa Ser Asn Leu
1               5

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
(A) NAME/KEY: Modified-site
(B) LOCATION: 3
(D) OTHER INFORMATION: /note="L-aminosuberic ester"

(ix) FEATURE:
(A) NAME/KEY: Modified-site
(B) LOCATION: 1
(D) OTHER INFORMATION: /note="tert-butoxycarbonyl"

(ix) FEATURE:
(A) NAME/KEY: Modified-site
(B) LOCATION: 1, 2 and 4
(D) OTHER INFORMATION: /note="benzyl"

(xi) SEQUENCE DESCRIPTION: SEQ ID NO:23:

Ser Thr Xaa Ser Asn Leu
1               5

(2) INFORMATION FOR SEQ ID NO:24:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (ix) FEATURE:
(A) NAME/KEY: Modified-site
(B) LOCATION: 2
(D) OTHER INFORMATION: /note="L-aminosuberic ester"

(ix) FEATURE:
(A) NAME/KEY: Modified-site
(B) LOCATION: 1
(D) OTHER INFORMATION: /note="tert-butoxycarbonyl"

(ix) FEATURE:
(A) NAME/KEY: Modified-site
(B) LOCATION: 1 and 3
(D) OTHER INFORMATION: /note="benzyl"

(ix) FEATURE:
(A) NAME/KEY: Modified-site
(B) LOCATION: 5
(D) OTHER INFORMATION: /note="phenacyl ester"

(xi) SEQUENCE DESCRIPTION: SEQ ID NO:24:

Thr Xaa Ser Asn Leu
1               5

(2) INFORMATION FOR SEQ ID NO:25:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (ix) FEATURE:
(A) NAME/KEY: Modified-site (B) LOCATION: 3
(D) OTHER INFORMATION: /note="L-aminosuberic ester"

(ix) FEATURE:
(A) NAME/KEY: Modified-site
(B) LOCATION: 1, 2 and 4
(D) OTHER INFORMATION: /note="benzyl"

(ix) FEATURE:
(A) NAME/KEY: Modified-site
(B) LOCATION: 6
(D) OTHER INFORMATION: /note="phenacyl ester"

(ix) FEATURE:
(A) NAME/KEY: Modified-site
(B) LOCATION: 1
(D) OTHER INFORMATION: /note="tert-butoxycarbonyl"

(xi) SEQUENCE DESCRIPTION: SEQ ID NO:25:

Ser Thr Xaa Ser Asn Leu
1               5

(2) INFORMATION FOR SEQ ID NO:26:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (ix) FEATURE:
(A) NAME/KEY: Modified-site
(B) LOCATION: 2
(D) OTHER INFORMATION: /note="L-aminosuberic ester"

(ix) FEATURE:
(A) NAME/KEY: Modified-site
(B) LOCATION: 1, 3 and 6
(D) OTHER INFORMATION: /note="benzyl"

(xi) SEQUENCE DESCRIPTION: SEQ ID NO:26:

Thr Xaa Ser Asn Leu Ser
1               5

(2) INFORMATION FOR SEQ ID NO:27:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (ix) FEATURE:
(A) NAME/KEY: Modified-site
(B) LOCATION: 2
(D) OTHER INFORMATION: /note="L-aminosuberic ester"

(ix) FEATURE:
(A) NAME/KEY: Modified-site
(B) LOCATION: 1
(D) OTHER INFORMATION: /note="tert-butoxycarbonyl"

(ix) FEATURE:
(A) NAME/KEY: Modified-site
(B) LOCATION: 1, 3 and 6
(D) OTHER INFORMATION: /note="benzyl"

( x i ) SEQUENCE DESCRIPTION: SEQ ID NO:27:

Thr Xaa Ser Asn Leu Ser
1                  5

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1 and 4
        ( D ) OTHER INFORMATION: /note="benzyl"

( i x ) FEATURE:
        ( A ) NAME/KEY: Modified-site
        ( B ) LOCATION: 1
        ( D ) OTHER INFORMATION: /note="tert-butoxycarbonyl"

( i x ) FEATURE:
        ( A ) NAME/KEY: Modified-site
        ( B ) LOCATION: 4
        ( D ) OTHER INFORMATION: /note="phenacyl ester"

( x i ) SEQUENCE DESCRIPTION: SEQ ID NO:28:

Ser Asn Leu Ser
1

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 2
        ( D ) OTHER INFORMATION: /note="L-aminosuberic ester"

( i x ) FEATURE:
        ( A ) NAME/KEY: Modified-site
        ( B ) LOCATION: 1
        ( D ) OTHER INFORMATION: /note="tert-butoxycarbonyl"

( i x ) FEATURE:
        ( A ) NAME/KEY: Modified-site
        ( B ) LOCATION: 1, 3 and 6
        ( D ) OTHER INFORMATION: /note="benzyl"

( x i ) SEQUENCE DESCRIPTION: SEQ ID NO:29:

Thr Xaa Ser Asn Leu Ser
1                  5

( 2 ) INFORMATION FOR SEQ ID NO:30:

( i ) SEQUENCE CHARACTERISTICS:
        ( A ) LENGTH: 6 amino acids
        ( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1
    ( D ) OTHER INFORMATION: /note="L-aminosuberic ester"

( i x ) FEATURE:
    ( A ) NAME/KEY: Modified-site
    ( B ) LOCATION: 2, 5 and 6
    ( D ) OTHER INFORMATION: /note="benzyl"

( x i ) SEQUENCE DESCRIPTION: SEQ ID NO:30:

Xaa Ser Asn Leu Ser Thr
1               5

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /note="L-aminosuberic ester"

( i x ) FEATURE:
        ( A ) NAME/KEY: Modified-site
        ( B ) LOCATION: 1
        ( D ) OTHER INFORMATION: /note="tert-butoxycarbonyl"

( i x ) FEATURE:
        ( A ) NAME/KEY: Modified-site
        ( B ) LOCATION: 2, 5 and 6
        ( D ) OTHER INFORMATION: /note="benzyl"

( x i ) SEQUENCE DESCRIPTION: SEQ ID NO:31:

Xaa Ser Asn Leu Ser Thr
1               5

( 2 ) INFORMATION FOR SEQ ID NO:32:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /note="tert-butoxycarbonyl"

( i x ) FEATURE:
        ( A ) NAME/KEY: Modified-site
        ( B ) LOCATION: 5

( D ) OTHER INFORMATION: /note="phenacyl ester"

( i x ) FEATURE:
                    ( A ) NAME/KEY: Modified-site
                    ( B ) LOCATION: 1, 4 and 5
                    ( D ) OTHER INFORMATION: /note="benzyl"

( x i ) SEQUENCE DESCRIPTION: SEQ ID NO:32:

Ser  Asn  Leu  Ser  Thr
         1                   5

( 2 ) INFORMATION FOR SEQ ID NO:33:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( i x ) FEATURE:
                    ( A ) NAME/KEY: Modified-site
                    ( B ) LOCATION: 1
                    ( D ) OTHER INFORMATION: /note="tert-butoxycarbonyl"

( i x ) FEATURE:
                    ( A ) NAME/KEY: Modified-site
                    ( B ) LOCATION: 1
                    ( D ) OTHER INFORMATION: /note="L-aminosuberic ester"

( i x ) FEATURE:
                    ( A ) NAME/KEY: Modified-site
                    ( B ) LOCATION: 2, 5 and 6
                    ( D ) OTHER INFORMATION: /note="benzyl"

( i x ) FEATURE:
                    ( A ) NAME/KEY: Modified-site
                    ( B ) LOCATION: 6
                    ( D ) OTHER INFORMATION: /note="phenacyl ester"

( x i ) SEQUENCE DESCRIPTION: SEQ ID NO:33:

Xaa  Ser  Asn  Leu  Ser  Thr
         1                        5

( 2 ) INFORMATION FOR SEQ ID NO:34:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( i x ) FEATURE:
                    ( A ) NAME/KEY: Modified-site
                    ( B ) LOCATION: 6
                    ( D ) OTHER INFORMATION: /note="L-aminosuberic ester"

( i x ) FEATURE:
                    ( A ) NAME/KEY: Modified-site
                    ( B ) LOCATION: 1, 4 and 5
                    ( D ) OTHER INFORMATION: /note="benzyl"

( x i ) SEQUENCE DESCRIPTION: SEQ ID NO:34:

Ser  Asn  Leu  Ser  Thr  Xaa
         1                   5

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /note=
          " 9-fluorenylmethyloxycarbonyl"

( i x ) FEATURE:
        ( A ) NAME/KEY: Modified-site
        ( B ) LOCATION: 4
        ( D ) OTHER INFORMATION: /note="L-aminosuberic acid ethyl
          ester"

( i x ) FEATURE:
        ( A ) NAME/KEY: Modified-site
        ( B ) LOCATION: 2, 3 and 5
        ( D ) OTHER INFORMATION: /note="tert-butyl"

( x i ) SEQUENCE DESCRIPTION: SEQ ID NO:35:

```
Leu  Ser  Thr  Xaa  Ser  Asn
1                   5
```

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1
        ( D ) OTHER INFORMATION: /note=
          " 9-fluorenylmethyloxycarbonyl"

( i x ) FEATURE:
        ( A ) NAME/KEY: Modified-site
        ( B ) LOCATION: 3
        ( D ) OTHER INFORMATION: /note="L-aminosuberic acid ethyl
          ester"

( i x ) FEATURE:
        ( A ) NAME/KEY: Modified-site
        ( B ) LOCATION: 1, 2 and 4
        ( D ) OTHER INFORMATION: /note="tert-butyl"

( x i ) SEQUENCE DESCRIPTION: SEQ ID NO:36:

```
Ser  Thr  Xaa  Ser  Asn
1              5
```

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
    ( A ) NAME/KEY: Modified-site
    ( B ) LOCATION: 1, 4 and 5
    ( D ) OTHER INFORMATION: /note="hydrogen atom
        or hydroxy- protecting group"

( x i ) SEQUENCE DESCRIPTION: SEQ ID NO:37:

Ser Asn Leu Ser Thr
1               5

( 2 ) INFORMATION FOR SEQ ID NO:38:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 1 and 4
        ( D ) OTHER INFORMATION: /note="hydrogen atom
            or hydroxy- protecting group"

( x i ) SEQUENCE DESCRIPTION: SEQ ID NO:38:

Ser Asn Leu Ser
1

( 2 ) INFORMATION FOR SEQ ID NO:39:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Modified-site
        ( B ) LOCATION: 3 and 4
        ( D ) OTHER INFORMATION: /note="hydrogen atom
            or hydroxy- protecting group"

( i x ) FEATURE:
        ( A ) NAME/KEY: Modified-site
        ( B ) LOCATION: 1
        ( D ) OTHER INFORMATION: /note="hydrogen atom
            or amino- protecting group"

( x i ) SEQUENCE DESCRIPTION: SEQ ID NO:39:

Asn Leu Ser Thr
1

( 2 ) INFORMATION FOR SEQ ID NO:40:

( i ) SEQUENCE CHARACTERISTICS:
        ( A ) LENGTH: 4 amino acids
        ( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (ix) FEATURE:
(A) NAME/KEY: Modified-site
(B) LOCATION: 1 and 3
(D) OTHER INFORMATION: /note="benzyl"

(ix) FEATURE:
(A) NAME/KEY: Modified-site
(B) LOCATION: 1
(D) OTHER INFORMATION: /note="tert-butoxycarbonyl"

(ix) FEATURE:
(A) NAME/KEY: Modified-site
(B) LOCATION: 2
(D) OTHER INFORMATION: /note="L-aminosuberic ester"

(xi) SEQUENCE DESCRIPTION: SEQ ID NO:40:

Thr Xaa Ser Asn
1

(2) INFORMATION FOR SEQ ID NO:41:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (ix) FEATURE:
(A) NAME/KEY: misc_feature
(B) LOCATION: 1
(D) OTHER INFORMATION: /note=is Lys, Thr or Ala (ix) FEATURE:
(A) NAME/KEY: misc_feature
(B) LOCATION: 2
(D) OTHER INFORMATION: /note=is Leu or Tyr (ix) FEATURE:
(A) NAME/KEY: misc_feature
(B) LOCATION: 3
(D) OTHER INFORMATION: /note=is Ser, Thr or Trp (ix) FEATURE:
(A) NAME/KEY: misc_feature
(B) LOCATION: 4
(D) OTHER INFORMATION: /note=is Gln, Lys or Arg (ix) FEATURE:
(A) NAME/KEY: misc_feature
(B) LOCATION: 5
(D) OTHER INFORMATION: /note=is Glu, Asp or Asn (ix) FEATURE:
(A) NAME/KEY: misc_feature
(B) LOCATION: 6
(D) OTHER INFORMATION: /note=is Leu or Phe (ix) FEATURE:
(A) NAME/KEY: misc_feature
(B) LOCATION: 7
(D) OTHER INFORMATION: /note=is His or Asn (ix) FEATURE:
(A) NAME/KEY: misc_feature
(B) LOCATION: 8

(D) OTHER INFORMATION: /note=is Lys or Asn (ix) FEATURE:
    (A) NAME/KEY: misc_feature
    (B) LOCATION: 9
    (D) OTHER INFORMATION: /note=is Leu, Phe or Thr (ix) FEATURE:
    (A) NAME/KEY: misc_feature
    (B) LOCATION: 10
    (D) OTHER INFORMATION: /note=is Gln or His (ix) FEATURE:
    (A) NAME/KEY: misc_feature
    (B) LOCATION: 11
    (D) OTHER INFORMATION: /note=is Thr or Arg (ix) FEATURE:
    (A) NAME/KEY: misc_feature
    (B) LOCATION: 12
    (D) OTHER INFORMATION: /note=is Tyr or Phe (ix) FEATURE:
    (A) NAME/KEY: misc_feature
    (B) LOCATION: 13
    (D) OTHER INFORMATION: /note=is Pro or Ser (ix) FEATURE:
    (A) NAME/KEY: misc_feature
    (B) LOCATION: 14
    (D) OTHER INFORMATION: /note=is Arg, Gly or Gln (ix) FEATURE:
    (A) NAME/KEY: misc_feature
    (B) LOCATION: 15
    (D) OTHER INFORMATION: /note=is Thr or Met (ix) FEATURE:
    (A) NAME/KEY: misc_feature
    (B) LOCATION: 16
    (D) OTHER INFORMATION: /note=is Asp, Ala, Asn or Gly (ix) FEATURE:
    (A) NAME/KEY: misc_feature
    (B) LOCATION: 17
    (D) OTHER INFORMATION: /note=is Val, Ile, Thr or Phe (ix) FEATURE:
    (A) NAME/KEY: misc_feature
    (B) LOCATION: 19
    (D) OTHER INFORMATION: /note=is Ala, Val, Pro or Ser (ix) FEATURE:
    (A) NAME/KEY: misc_feature
    (B) LOCATION: 20
    (D) OTHER INFORMATION: /note=is Gly or Glu (ix) FEATURE:
    (A) NAME/KEY: misc_feature
    (B) LOCATION: 21
    (D) OTHER INFORMATION: /note=is Thr or Ala (ix) FEATURE:
    (A) NAME/KEY: misc_feature
    (B) LOCATION: 22
    (D) OTHER INFORMATION: /note=is attached to a resin support (xi) SEQUENCE DESCRIPTION: SEQ ID NO:41:

Xaa Xaa Xaa Xaa Xaa Xaa Xaa Xaa Xaa Xaa Xaa Xaa Xaa Xaa Xaa Xaa
1               5                   10                  15

Xaa Gly Xaa Xaa Xaa Pro
        20

(2) INFORMATION FOR SEQ ID NO:42:

( i ) SEQUENCE CHARACTERISTICS:
   ( A ) LENGTH: 25 amino acids
   ( B ) TYPE: amino acid
   ( C ) STRANDEDNESS: single
   ( D ) TOPOLOGY: linear ( i i ) MOLECULE TYPE: peptide ( i i i ) HYPOTHETICAL: NO ( i v ) ANTI-SENSE: NO ( i x ) FEATURE:
   ( A ) NAME/KEY: misc_feature
   ( B ) LOCATION: 1
   ( D ) OTHER INFORMATION: /note=is Val or Met ( i x ) FEATURE:
   ( A ) NAME/KEY: misc_feature
   ( B ) LOCATION: 3
   ( D ) OTHER INFORMATION: /note=is Ser or Gly ( i x ) FEATURE:
   ( A ) NAME/KEY: misc_feature
   ( B ) LOCATION: 4
   ( D ) OTHER INFORMATION: /note=is Lys, Thr or Ala ( i x ) FEATURE:
   ( A ) NAME/KEY: misc_feature
   ( B ) LOCATION: 5
   ( D ) OTHER INFORMATION: /note=is Leu or Tyr ( i x ) FEATURE:
   ( A ) NAME/KEY: misc_feature
   ( B ) LOCATION: 6
   ( D ) OTHER INFORMATION: /note=is Ser, Thr or Trp ( i x ) FEATURE:
   ( A ) NAME/KEY: misc_feature
   ( B ) LOCATION: 7
   ( D ) OTHER INFORMATION: /note=is Gln, Lys or Arg ( i x ) FEATURE:
   ( A ) NAME/KEY: misc_feature
   ( B ) LOCATION: 8
   ( D ) OTHER INFORMATION: /note=is Glu, Asp or Asn ( i x ) FEATURE:
   ( A ) NAME/KEY: misc_feature
   ( B ) LOCATION: 9
   ( D ) OTHER INFORMATION: /note=is Leu or Phe ( i x ) FEATURE:
   ( A ) NAME/KEY: misc_feature
   ( B ) LOCATION: 10
   ( D ) OTHER INFORMATION: /note=is His or Asn ( i x ) FEATURE:
   ( A ) NAME/KEY: misc_feature
   ( B ) LOCATION: 11
   ( D ) OTHER INFORMATION: /note=is Lys or Asn ( i x ) FEATURE:
   ( A ) NAME/KEY: misc_feature
   ( B ) LOCATION: 12
   ( D ) OTHER INFORMATION: /note=is Leu, Phe or Thr ( i x ) FEATURE:
   ( A ) NAME/KEY: misc_feature
   ( B ) LOCATION: 13
   ( D ) OTHER INFORMATION: /note=is Gln or His ( i x ) FEATURE:
   ( A ) NAME/KEY: misc_feature
   ( B ) LOCATION: 14
   ( D ) OTHER INFORMATION: /note=is Thr or Arg ( i x ) FEATURE:
   ( A ) NAME/KEY: misc_feature
   ( B ) LOCATION: 15
   ( D ) OTHER INFORMATION: /note=is Tyr or Phe -continued ( i x ) FEATURE:
    ( A ) NAME/KEY: misc_feature
    ( B ) LOCATION: 16
    ( D ) OTHER INFORMATION: /note=is Pro or Ser ( i x ) FEATURE:
    ( A ) NAME/KEY: misc_feature
    ( B ) LOCATION: 17
    ( D ) OTHER INFORMATION: /note=is Arg, Gly or Gln ( i x ) FEATURE:
    ( A ) NAME/KEY: misc_feature
    ( B ) LOCATION: 18
    ( D ) OTHER INFORMATION: /note=is Thr or Met ( i x ) FEATURE:
    ( A ) NAME/KEY: misc_feature
    ( B ) LOCATION: 19
    ( D ) OTHER INFORMATION: /note=is Asp, Ala, Asn or
        Gly ( i x ) FEATURE:
    ( A ) NAME/KEY: misc_feature
    ( B ) LOCATION: 20
    ( D ) OTHER INFORMATION: /note=is Val, Ile, Thr or
        Phe ( i x ) FEATURE:
    ( A ) NAME/KEY: misc_feature
    ( B ) LOCATION: 22
    ( D ) OTHER INFORMATION: /note=is Ala, Val, Pro or
        Ser ( i x ) FEATURE:
    ( A ) NAME/KEY: misc_feature
    ( B ) LOCATION: 23
    ( D ) OTHER INFORMATION: /note=is Gly or Glu ( i x ) FEATURE:
    ( A ) NAME/KEY: misc_feature
    ( B ) LOCATION: 24
    ( D ) OTHER INFORMATION: /note=is Thr or Ala ( i x ) FEATURE:
    ( A ) NAME/KEY: misc_feature
    ( B ) LOCATION: 25
    ( D ) OTHER INFORMATION: /note=is a prolinamide ( x i ) SEQUENCE DESCRIPTION: SEQ ID NO:42:

```
Xaa Leu Xaa Xaa Xaa Xaa Xaa Xaa Xaa Xaa Xaa Xaa Xaa Xaa Xaa Xaa
 1               5                  10                  15

Xaa Xaa Xaa Xaa Gly Xaa Xaa Xaa Pro
            20              25
```

( 2 ) INFORMATION FOR SEQ ID NO:43:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( i x ) FEATURE:
        ( A ) NAME/KEY: Cross-links
        ( B ) LOCATION: join(1..6)
        ( D ) OTHER INFORMATION: /note="L-aminosuberic acid forms a
            linkage between positions 1 and 6"

( i x ) FEATURE:
        ( A ) NAME/KEY: Modified-site
        ( B ) LOCATION: 1, 4, 5, 12, 20, 24 and 30
        ( D ) OTHER INFORMATION: /note="benzyl"

( i x ) FEATURE:
    ( A ) NAME/KEY: Modified-site
    ( B ) LOCATION: 14 and 25
    ( D ) OTHER INFORMATION: /note="benzyl ester"

( i x ) FEATURE:
    ( A ) NAME/KEY: Modified-site
    ( B ) LOCATION: 16 and 23
    ( D ) OTHER INFORMATION: /note="tosyl"

( i x ) FEATURE:
    ( A ) NAME/KEY: Modified-site
    ( B ) LOCATION: 21
    ( D ) OTHER INFORMATION: /note="2-bromobenzyloxycarboxyl"

( i x ) FEATURE:
    ( A ) NAME/KEY: Modified-site
    ( B ) LOCATION: 10 and 17
    ( D ) OTHER INFORMATION: /note="2-chlorobenzyloxycarboxyl"

( x i ) SEQUENCE DESCRIPTION: SEQ ID NO:43:

```
Ser Asn Leu Ser Thr Xaa Val Leu Gly Lys Leu Ser Gln Glu Leu His
 1               5                  10                      15

Lys Leu Gln Thr Thr Pro Arg Thr Asp Val Gly Ala Gly Thr Pro
         20                  25                  30
```

( 2 ) INFORMATION FOR SEQ ID NO:44:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:44:

```
Ser Asn Leu Ser Thr
 1               5
```

( 2 ) INFORMATION FOR SEQ ID NO:45:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:45:

```
Ser Asn Leu Ser
 1
```

( 2 ) INFORMATION FOR SEQ ID NO:46:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO (x i) SEQUENCE DESCRIPTION: SEQ ID NO:46:

Asn Leu Ser Thr
1

(2) INFORMATION FOR SEQ ID NO:47:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (x i) SEQUENCE DESCRIPTION: SEQ ID NO:47:

Ser Asn Leu Ser Thr
1               5

PEPTIDES AND PROCESSES FOR PRODUCING CYCLIC PEPTIDES

CROSS-REFERENCE TO RELATED APPLICATIONS

This application is a continuation-in-part of co-pending international application PCT/JP90/01440 filed Nov. 7, 1990, the United States of America having been designated, and claiming the priority of Japanese patent application 290660/1989, filed Nov. 8, 1989, both of which earlier applications are incorporated herein by reference.

FILED OF THE INVENTION

The present invention relates to peptides and processes for producing cyclic peptides. More particularly, the invention relates to peptides which are useful for the production of cyclic peptides, such as a synthetic calcitonin derivative (elcatonin) of the following formula (SEQ ID NO: 1);

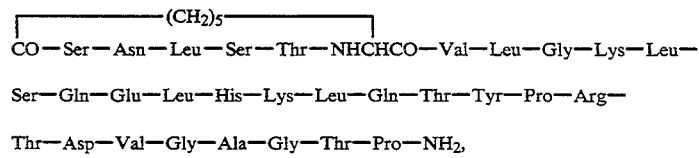

or acid addition salts or complex compounds thereof and to novel processes for producing cyclic peptides.

BACKGROUND OF THE INVENTION

Calcitonin is known as a polypeptide having useful pharmacologic activities such as potent hypocalcemic and hypophosphatemic activities, bone formation-stimulating and bone resorption-inhibiting activities, urinary phosphate excretion-promoting activity and so on. Calcitonin has been isolated, by extraction, from the thyroids of various mammalian animals inclusive of man and the ultimobranchial bodies of fish, cyclostomes and fowls and its primary amino acid sequence has been established. Based on this amino acid sequence, a number of synthetic calcitonin analogs have been synthesized and reported. All the known species of calcitonin of animal origin are polypeptides consisting of 32 amino acids each, with the 1- and 7-positions thereof being invariably L-cysteine residues whose mercapto groups are bound to each other to form a disulfide linkage and the carboxy-terminal amino acid residue being prolinamide. Because of the presence of said disulfide linkage within the molecule, these naturally-occurring calcitonins are not as stable in solution as desired.

Therefore, a process for producing a synthetic calcitonin has been developed in which L-cysteine resides in positions-1 and -7 are replaced with α-L-aminosuberic acid of the following formula:

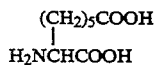

In this process, a peptide of the formula (SEQ ID NO: 2);

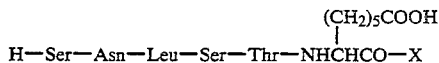

(wherein X means a hydroxyl group, a carboxy-protecting group which is commonly used in peptide chemistry or an amino acid residue or peptide residue which is necessary to form calcitonin, and each amino acid residue may be protected with a protective group commonly used in peptide chemistry) is subjected to cyclization in liquid phase and the necessary fragments are further coupled thereto in liquid phase (hereinafter referred to as liquid phase synthesis) to synthesize the desired calcitonin derivative [Japanese Patent Publication No. 41677/1978, Japanese Patent Laid-open No. 112099/1986, Japanese Patent Laid-open No. 203699/1988 and Farumashia Review No. 3 "Seeking New Drugs—Physiologically Active Peptides" (edited by Farumashia Review Committee), P. 153–154].

In this and other processes, however, the solubility of the peptide varies delicately as the number of constituent amino acids increases, so that it becomes increasingly difficult to find an appropriate solvent. Moreover, owing to this very fact, the difficulty of fractionation of the desired polypeptide from the unreacted starting compounds and by-products is also increased. Particularly in the cyclization reaction, formation of by-products must be suppressed to a minimum. Therefore, the conventional method for liquid-phase synthesis of calcitonin is low in yield and cannot be considered to be commercially acceptable.

It is, therefore, an object of the present invention to provide peptides or acid addition salts or complex compounds thereof, which are useful for the production of cyclic peptides, particularly elcatonin which is a calcitonin derivative.

It is another object of the invention to provide novel and commercially useful processes for producing cyclic peptides, particularly elcatonin which is a calcitonin derivative, in good yield.

SUMMARY OF THE INVENTION

The intensive research of the inventors for accomplishing the above-mentioned objects revealed that these objects can be accomplished by the following new schemes. Thus, (1) the side-chain carboxyl group of α-L-aminosuberic acid is not directly condensed with the amino group of the N-terminal amino group for cyclization but using a peptide prepared by condensing an amino acid or peptide to at least the side-chain carboxyl group of α-L-aminosuberic acid or an acid addition salt or complex thereof, the cyclization reaction between the C-terminal carboxyl group and the amino group of the N-terminal amino acid is carried out, (2) the cyclization reaction is conducted in the presence of an alkali metal salt, and (3) the techniques of liquid phase synthesis and solid phase synthesis are utilized in suitable combinations. The present invention is predicated on the above findings. Thus, the present invention provides a peptide of the following general formula (I):

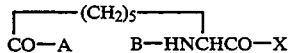
(I)

(wherein A means Ser(X1)-Asn-Leu-Ser(X1)-Thr(X1)-OH (SEQ ID NO: 37), Ser(X1)-Asn-Leu-Ser(X1)-OH (SEQ ID NO: 38), Ser(X1)-Asn-Leu-OH, Ser(X1)-Asn-OH or Ser(X1)-OH; B means X2, X2-Thr(X1), X2-Ser(X1)-Thr(X1), X2-Leu-Ser(X1)-Thr(X1) or X2-Asn-Leu-Ser(X1)-Thr(X1) (SEQ ID NO: 39); X means a hydroxyl group, a carboxy-protecting group, an amino acid residue or a peptide residue; each amino acid residue may be protected with a protective group; X1 means a hydrogen atom or a hydroxy-protecting group; and X2 means a hydrogen atom or an amino-protecting group) or an acid addition salt or complex compound thereof.

In accordance with the present invention, a cyclic peptide of the following general formula (II) (SEQ ID NO: 3):

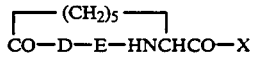
(II)

(wherein D-E means Ser-Asn-Leu-Ser-Thr (SEQ ID NO: 44); X means a hydroxyl group, a carboxy-protecting group, an amino acid residue or a peptide residue; each amino acid residue may be protected with a protective group) or an acid addition salt or complex compound thereof is synthesized as follows.

(1) A production process in which a peptide of the general formula (III):

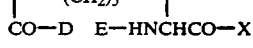
(III)

(wherein D means Ser-OH, Ser-Asn-OH, Ser-Asn-Leu-OH, Ser-Asn-Leu-Ser-OH (SEQ ID NO: 45) or Ser-Asn-Leu-Ser-Thr-OH (SEQ ID NO: 44); E means H-Asn-Leu-Ser-Thr (SEQ ID NO: 46), H-Leu-Ser-Thr, H-Ser-Thr, H-Thr or a hydrogen atom; each amino acid residue may have been protected with a protective group; X is as defined hereinbefore) is subjected to cyclization reaction, preferably cyclization by chemical condensation.

(2) A production process in which a peptide of the general formula (IV):

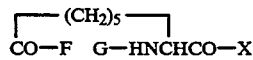
(IV)

(wherein F means a hydroxyl group, an active ester residue, Ser-OH, Ser-Asn-OH, Ser-Asn-Leu-OH, Ser-Asn-Leu-Ser-OH (SEQ ID NO: 45) or Ser-Asn-Leu-Ser-Thr-OH (SEQ ID NO: 44); G means H-Ser-Asn-Leu-Ser-Thr (SEQ ID NO: 44), H-Asn-Leu-Ser-Thr (SEQ ID NO: 46), H-Leu-Ser-Thr, H-Ser-Thr, H-Thr or a hydrogen atom; each amino acid residue may have been protected with a protective group; X is as defined hereinbefore) is subjected to cyclization reaction in the presence of an alkali metal salt. In this production process, the side-chain carboxyl group of α-L-aminosuberic acid may not have been condensed to an amino acid or peptide.

The present invention further provides a process for producing a cyclic peptide or an acid addition salt or complex compound thereof which comprises condensing a peptide of the general formula (V) (SEQ ID NO: 4):

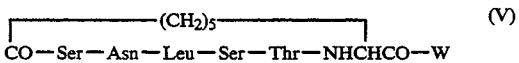
(V)

[wherein W means a hydroxyl group or a peptide residue of the general formula (VII):

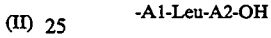
(VII)

(where A1 means Val or Met; A2 means Ser or Gly); each amino acid residue may have been protected with a protective group] with a peptide-resin synthesized on a solid phase reaction resin and having the following general formula (VI): by the technique of solid phase synthesis.

Xaa Xaa Xaa Xaa Xaa Xaa Xaa Xaa Xaa Xaa Xaa Xaa Xaa Xaa Xaa Xaa
1           5                   10                  15
Xaa Gly Xaa Xaa Xaa Pro   (SEQ ID NO: 41)   (VI)
        20 wherein:
Xaa at position 1 is Lys, Thr or Ala; Xaa at position 2 is Leu or Tyr; Xaa at position 3 is Ser, Thr or Trp; Xaa at position 4 is Gln, Lys or Arg; Xaa at position 5 is Glu, Asp or Asn; Xaa at position 6 is Leu or Phe; Xaa at position 7 is His or Asn; Xaa at position 8 is Lys or Asn; Xaa at position 9 is Leu, Phe or Thr; Xaa at position 10 is Gln or His; Xaa at position 11 is Thr or Arg; Xaa at position 12 is Tyr or Phe; Xaa at position 13 is Pro or Ser; Xaa at position 14 is Arg, Gly or Gln; Xaa at position 15 is Thr or Met; Xaa at position 16 is Asp, Ala, Asn or Gly; Xaa at position 17 is Val, Ile, Thr or Phe; Xaa at position 19 is Ala, Val, Pro or Ser; Xaa at postion 20 is Gly or Glu; Xaa at position 21 is Thr or Ala; and Pro at position 22 is attached to a resin support;
or as Xaa Leu Xaa Xaa Xaa Xaa Xaa Xaa Xaa Xaa Xaa Xaa Xaa Xaa Xaa Xaa
1           5                   10                  15
Xaa Xaa Xaa Xaa Gly Xaa Xaa Xaa Pro   (SEQ ID NO: 42)   (VIII)
        20              25 wherein:
Xaa at position 1 is Val or Met; Xaa at position 3 is Ser or Gly; Xaa at position 4 is Lys, Thr or Ala; Xaa at position 5 is Leu or Tyr; Xaa at position 6 is Ser, Thr or Trp; Xaa at position 7 is Gln, Lys or Arg; Xaa at position 8 is Glu, Asp or Asn; Xaa at position 9 is Leu or Phe; Xaa at position 10 is His or Asn; Xaa at position 11 is Lys or Asn; Xaa at position 12 is Leu, Phe or Thr; Xaa at position 13 is Gln or His; Xaa at position 14 is Thr or Arg; Xaa at position 15 is Tyr or Phe; Xaa at position 16 is Pro or Ser; Xaa at position 17 is Arg, Gly or Gln; Xaa at position 18 is Thr or Met; Xaa at position 19 is Asp, Ala, Asn or Gly; Xaa at position 20 is Val, Ile, Thr or Phe; Xaa at position 22 is Ala, Val, Pro or Ser; Xaa at position 23 is Gly or Glu; Xaa at position 24 is Thr or Ala; and Pro at position 25 is attached to a resin support;

each amino acid residue may have been protected with a protective group; provided, however, that when W is a hydroxyl group, SEQ ID NO: 42 is used and when W is -A1-Leu-A2-OH, SEQ ID NO: 41 is used. (The resin means a support resin for solid phase reaction.)

In this specification, the abbreviations used to denote amino acids, peptides, protective groups, solvents, etc. are those specified by IUPAC-IUB or those commonly used in the relevant field of chemistry. The following is a partial list of such abbreviations: (It should also be noted that where any amino acid or the like may exist as optical isomers, the L-form is invariably meant unless otherwise indicated.)

Ala: Alanine
Arg: Arginine
Asn: Asparagine
Asp: Aspartic acid
Gln: Glutamine
Glu: Glutamic acid
Gly: Glycine
His: Histidine
Ile: Isoleucine
Leu: Leucine
Lys: Lysine
Met: Methionine
Phe: Phenylalanine
Pro: Proline
Ser: Serine
Thr: Threonine
Tyr: Tyrosine
Val: Valine
Boc: tert-Butoxycarbonyl
Bzl: Benzyl
Z: Benzyloxycarbonyl
Tos: Tosyl
Cl-Z: 2-Chlorobenzyloxycarbonyl
Br-Z: 2-Bromobenzyloxycarbonyl
OMe: Methyl ester
OPac: Phenacyl ester
OBzl: Benzyl ester
OSu: N-Hydroxysccinimide ester
HOSu: N-Hydroxysuccinimide
TFA: Trifluoroacetic acid
THF: Tetrahydrofuran
DMF: N,N-Dimethylformamide
DMSO: Dimethyl sulfoxide
NMP: N-Methylpyrrolidone
DCC: Dicyclohexylcarbodiimide
WSC: N-Ethyl-N'-dimethylaminopropylcarbodiimide
HOBt: 1-Hydroxybenzotriazole.

DETAILED DESCRIPTION OF THE INVENTION

The peptide of general formula (I) provided in accordance with the present invention has an amino acid or peptide condensed to at least the side-chain carboxyl group of α-L-aminosuberic acid.

The combination of A and B in the peptide of general formula (I) can be selected according to the desired species of cyclic peptide. In their preferred combination, A and B form a peptide of the formula Ser(X1)-Asn-Leu-Ser(X1)-Thr(X1) (SEQ ID NO: 37). The preferred combinations of A and B are as follows:

(1) A: Ser(X1)-Asn-Leu-Ser(X1)-Thr(X1)-OH (SEQ ID NO: 37)
B: X2

(2) A: Ser(X1)-Asn-Leu-Ser(X1)-OH (SEQ ID NO: 38)
B: X2-Thr(X1)

(3) A: Ser(X1)-Asn-Leu-OH
B: X2-Ser(X1)-Thr(X1)

(4) A: Ser(X1)-Asn-OH
B: X2-Leu-Ser(X1)-Thr(X1)

(5) A: Ser(X1)-OH
B: X2-Asn-Leu-Ser(X1)-Thr(X1) (SEQ ID NO: 39)

(wherein X1 and X2 are as defined hereinbefore).

The preferred combination of D and E in general formula (III) and that of F and G in general formula (IV), like the aforesaid combination of A and B, form the peptide Ser-Asn-Leu-Ser-Thr (SEQ ID NO: 44). However, F in general formula (IV), unlike D in general formula (III), may optionally be a hydroxy group or an active ester residue.

Referring to general formulas (I) through (IV), the carboxy-protecting group represented by X may generally be any of those used commonly in peptide chemistry. Among such carboxy-protecting groups are, for example, alkoxy groups such as methoxy, ethoxy, propyloxy, isopropyloxy, butyloxy, iso-butyloxy, sec-butyloxy, tert-butyloxy, etc.; cyloalkyloxy groups such as cyclohexyloxy etc.; aralkyloxy groups which may optionally be substituted, such as benzyloxy, p-methoxybenzyloxy, p-nitrobenzyloxy, p-chlorobenzyloxy, p-bromobenzyloxy, benzhydryloxy, etc.; substituted hydrazino groups such as carbobenzoxyhydrazino, tert-butyloxycarbonylhydrazino, tritylhydrazino, etc.; and phenacyl.

Referring, further, to general formulas (I) through (IV), the calcitonin-forming amino acid residue among the amino acid residues represented by X include, for example, Val-OH and Met-OH. The peptide residue X is not particularly limited only if it is a calcitonin-forming peptide residue. The peptide residue includes, among others, a lower peptide residue of the general formula (VII):

-A1-Leu-A2-OH   (VII)

and a peptide residue of the following general formula (VIII):

Xaa Leu Xaa Xaa Xaa Xaa Xaa Xaa Xaa Xaa Xaa Xaa Xaa Xaa Xaa
1           5                    10                  15
Xaa Xaa Xaa Xaa Gly Xaa Xaa Xaa Pro   (SEQ ID NO: 42)
20                        25 or a fragment thereof, wherein: Xaa at position 1 is Val or Met; Xaa at position 3 is Ser or Gly; Xaa at position 4 is Lys, Thr or Ala; Xaa at position 5 is Leu or Tyr; Xaa at position 6 is Ser, Thr or Trp; Xaa at position 7 is Gln, Lys or Arg; Xaa at position 8 is Glu, Asp or Asn; Xaa at position 9 is Leu or Phe; Xaa at position 10 is His or Asn; Xaa at position 11 is Lys or Asn; Xaa at position 12 is Leu, Phe or Thr; Xaa at position 13 is Gln or His; Xaa at position 14 is Thr or Arg; Xaa at position 15 is Tyr or Phe; Xaa at position 16 is Pro or Ser; Xaa at position 17 is Arg, Gly or Gln; Xaa at position 18 is Thr or Met; Xaa at position 19 is Asp, Ala, Asn or Gly; Xaa at position 20 is Val, Ile, Thr or Phe; Xaa at position 22 is Ala, Val, Pro or Ser; Xaa at position 23 is Gly or Glu; Xaa at position 24 is Thr or Ala; and Pro at position 25 is a prolinamide.

The aforesaid calcitonin-forming amino acid residue, peptide residue of general formula (VII), namely -A1-Leu-A2, and peptides corresponding to fragments of the peptide residue of general formula (VIII) are suitable synthetic intermediates for calcitonin.

Referring to the lower peptide residue of general formula (VII), a preferred calcitonin-forming peptide residue is -Val-Leu-Gly-OH. Referring to the peptide residue of general formula (VIII), a preferred calcitonin-forming peptide residue is (SEQ ID NO: 5) -Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH$_2$.

In the peptides represented by general formulas (I) through (VI), respectively, the protective groups for respective amino acid residues can be those used commonly in peptide chemistry.

Thus, among such common protective groups, the carboxy-protecting groups may be those mentioned for X.

The amino-protecting groups include, for example, alkoxycarbonyl groups which may optionally be substituted, such as Boc, trichloroethyloxycarbonyl, tert-amyloxycarbonyl, 9-fluorenylmethyloxycarbonyl, etc.; cycloalkyloxycarbonyl groups which may optionally be substituted, such as cyclopentyloxycarbonyl, cyclohexyloxycarbonyl, etc.; aralkyloxycarbonyl groups which may optionally be substituted, such as Z, p-methoxybenzyloxycarbonyl, Cl-Z, p-chlorobenzyloxycarbonyl, Br-Z, p-bromobenzyl-oxycarbonyl, p-nitrobenzyloxycarbonyl, adamantyloxy-carbonyl, etc.; aralkyl groups which may optionally be substituted, such as Bzl, benzhydryl, trityl, etc.; and acyl groups which may optionally be substituted, such as trifluoroacetyl, phthalyl, formyl, benzenesulfonyl, Tos, o-nitrophenylsulfenyl, 2,4-dinitrophenylsulfenyl, diphenylphosphinothioyl and so on.

The guanidino group of Arg may be protected with, for example, nitro group, Z or Tos. This guanidino group need not necessarily be protected.

The imidazolyl group of His need not necessarily be protected but may be protected with, for example, Bzl, TOS, Z, trityl, adamantyloxycarbonyl, 2,2,2-trifluoro-1-tert-butoxycarbonylaminoethyl, 2,2,2-trifluoro-1-benzyloxycarbonylaminoethyl or the like.

The hydroxyl group of Ser, Thr or Tyr may be protected with, for example, Bzl, 4-methoxybenzyl, 4-methylbenzyl, 3,4-dimethylbenzyl, 4-chlorobenzyl, 2,6-dichlorobenzyl, 4-nitrobenzyl, benzhydryl, Z, Cl-Z, Br-Z, tetrahydropyranyl or the like. This hydroxyl group need not necessarily protected.

The peptides represented by general formula (I), (III) and (IV), respectively, can each be synthesized by repeating protection, deprotection of the protective group or groups and condensation reactions in the well-known manner of peptide synthesis. Thus, as the protective groups for the starting and intermediate compounds used in the practice of the present invention, those protective groups which can be easily eliminated by the means well-established in peptide synthesis, such as hydrolysis, acidolysis, reduction, aminolysis, hydrazinolysis, etc. can be utilized.

Among the peptides represented by general formulas (I), (III) and (IV), respectively, those peptides in which X is a hydroxy group or a carboxy-protective group can each be synthesized by, for example, serial condensation of the corresponding amino acids or condensation of a peptide comprising of 2 to 5 amino acid to the side-chain carboxyl group and/or amino group of an L-aminosuberic acid-α-lower alkyl ester. However, where B or E in the peptide of general formula (I) or (III) is a hydrogen atom and where G in the peptide of general formula (IV) is a hydrogen atom, the amino group of the L-aminosuberic acid α-lower alkyl ester must be previously protected. Moreover, where F in the peptide of general formula (IV) is a hydroxyl group, the side-chain carboxyl group of the L-aminosuberic acid-α-lower alkyl ester is preferably protected.

Specifically, among peptides of the general formula (I), the peptide which can be represented by the following formula (SEQ ID NO: 6):

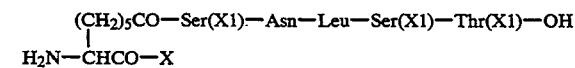

(wherein X1 is Bzl; X is a carboxy-protecting group) can be synthesized by the following process, for instance. Thus, N-protected leucylserine is condensed to threonine by the conventional procedure of peptide synthesis, for example the active ester method, mixed acid anhydride method or the DCC-HOBt method. Then, N-protected serylasparagine and N-protected aminosuberic acid-α-lower alkyl ester are serially condensed to the resulting tripeptide and the protective group on the N-protected aminosuberic acid-α-lower alkyl ester is then eliminated to give the desired peptide. Preferably, the carboxyl group of threonine is first protected with a protective group and this protective group is eliminated after the above condensation with the amino acids and peptide.

Among the peptides of general formula (III) which are employed in the present invention, peptides of the following formula (SEQ ID NO: 7):

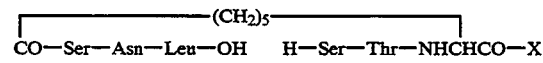

(wherein X is a carboxy-protecting group) can be synthesized by the following process, for instance. Thus, N-protected threonine is condensed with L-aminosuberic acid-α-lower alkyl ester by the active ester method, mixed acid anhydride method or the like and the side-chain carboxyl group of the L-aminosuberic acid is then activated and condensed with serylaspara-gylleucine. Then, N-protected serine is condensed with the resulting pentapeptide by the conventional procedure of peptide synthesis, for example the mixed acid anhydride method, the active ester method or the like, and finally the protective group of the N-protected serine is eliminated to give the desired peptide.

Among the peptides represented by general formulas (I), (III) and (IV), respectively, the peptides in which X is an amino acid residue or a peptide residue can be obtained as follows, for instance. Thus, the alkoxy group protecting the L-aminosuberic acid-α-lower alkyl ester condensed with the amino acid or peptide as above is first eliminated, the carboxyl group is then activated as aforesaid, and the corresponding amino acid is condensed or amino acids are serially condensed, or peptide comprising of two or more amino acids is condensed, to give the desired peptide.

In the condensation reaction, (a) an amino acid or peptide having an activated terminal carboxyl group and a protected α-amino group with a protective group can be reacted with an amino acid or peptide having a free α-amino group and a protected carboxyl group with a protective group or, alternatively, (b) an amino acid or peptide having an activated α-amino group and a protected carboxyl group can be reacted with an amino acid or peptide having a free carboxyl group and a protected α-amino group.

The carboxyl group can be activated in the form of, for example, an acid azide, acid anhydride, acid imidazolide or active ester, or by treatment with, for example, a carbodiimide, N,N'-carbonyldiimidazole or isoxazolium salt, e.g. Woodward's reagent. The active ester includes, for example, the cyanomethyl ester, thiophenyl ester, p-nitrothiophenyl ester, p-methanesulfonylphenyl ester, p-nitrophenyl ester, 2,4-dinitrophenyl ester, 2,4,6-trichlorophenyl ester, pentachlorophenyl ester, OSu, N-hydroxyphthalimide ester, 8-hydroxyquinoline ester and N-hydroxypiperidine ester.

The preferred methods for condensation are the carbodiimide method, azide method, active ester method and mixed acid anhydride method. Still preferred condensation reactions are those with inhibited racemization in the course of condensation, such as the active ester method, the carbodiimide method or a combination thereof, such as the DCC-HOSu method or the DCC-HOBt method.

The process for producing a cyclic peptide of general formula (II) from a peptide of general formula (III) is characterized in that the activated carboxyl group of the C-terminal amino acid of peptide (III) and the amino group of the N-terminal amino acid thereof are subjected to condensation-cyclization reaction. This cyclization reaction of the peptide (III) to give the peptide (II) can be conducted by the usual procedure of chemical condensation reaction. Preferably, this cyclization reaction is conducted in the presence of an alkali metal salt.

The process for producing a cyclic peptide of general formula (II) from a peptide of general formula (IV) is characterized in that the peptide (IV) is cyclized in the presence of an alkali metal salt to give the peptide (II). When F in the peptide of general formula (IV) is a hydroxyl group or an active ester residue, this cyclization reaction can be carried out by condensing the activated side-chain carboxyl group of α-L-aminosuberic acid with the amino group of the N-terminal amino acid. In this reaction, the hydroxyl groups of Ser and Thr are preferably protected beforehand. In the presence of an alkali metal salt, the cylization reaction can be smoothly conducted even when F in the peptide of general formula (IV) is a hydroxyl group or an active ester residue, thus contributing to an increased peptide yield.

The alkali metal salt mentioned above includes the halides, e.g. fluoride, chloride, bromide and iodide, of lithium, sodium, potassium, rubidium or cesium, for instance. These alkali metal salts can be used either alone or in an appropriate combinaion.

The proportion of the alkali metal salt is not critical unless smooth cyclization is interferred with but generally may range from about 0.01 to 400 equivalents, preferably about 0.01 to 100 equivalents, based on the peptide to be cyclized. Thus, assuming that the alkali metal salt is a mixture of lithium chloride, sodium chloride, potassium chloride and cesium chloride, each of these salts may be added in a proportion of about 0.1 to 100 equivalents, preferably about 0.1 to 20 equivalents relative to the peptide to be cyclized.

Where, in the synthesis of a cyclic peptide of general formula (II), an amino acid or peptide whose active group or groups have been protected, the product peptide protected with the protective group or groups are subjected to deprotection by the routine procedure, preferably with an acid, e.g. hydrogen fluoride, to obtain the desired cyclic peptide.

It is preferable that W in the cyclic peptide of general formula (V) and Y in the peptide-resin of general formula (VI) each be a constituent of elcatonin. Thus, (a) when W is a hydroxyl group, Y is preferably H-Val-Leu-Gly- and (b) when W is -Val-Leu-Gly-OH, Y is preferably a hydrogen atom. The preferred combination of W and Y is the combination designated as (b) above. Furthermore, the preferred peptide-resin of general formula (VI) (SEQ ID NO: 8) is Y-Lys-Leu-Ser-Gln-Glu-Leu-His-Lys-Leu-Gln-Thr-Tyr-Pro-Arg-Thr-Asp-Val-Gly-Ala-Gly-Thr-Pro-Resin.

This production process is characterized in that a peptide of general formula (V) is reacted with a peptide of general formula (VI) synthesized by solid phase synthesis on the solid phase resin to give a cyclic peptide, particularly elcatonin. More particularly, the cyclic peptide of general formula (V), namely the fragment comprising of amino acids from position 1 to position 6 or from position 1 to position 9, is condensed with the peptide of general formula (VI), namely the peptide comprising of amino acids from position 7 to position 31 or from position 10 to position 31 on the solid phase reaction resin by the technique of solid phase synthesis. The C-terminal amino acid of the fragment of general formula (V) is preferably glycine in view of condensation reactivity and for prevention of racemization. Therefore, elcatonin is preferably synthesized by condensing the peptide comprising of the amino acids in positions 1 through 9, which is among the cyclized peptides of general formula (V), with the peptide comprising of the amino acids in positions 10 through 31 on the solid phase reaction resin which is among the peptides of general formula (VI).

The above peptide on solid phase reaction resin, represented by general formula (VI), can be synthesized in accordance with the method developed by R. B. Merrifield, J. Am. Chem. Soc., 85, 2149 (1963), namely by serial condensation of amino acids, whose functional groups have been previously protected with appropirate protective groups, from the C-terminal by utilizing the symmetric acid anhydride method, active ester method and other methods.

The support resin for solid phase synthesis is not particularly limited in kind but in view of the fact that the C-terminal of the desired peptide is an acid amide, there may be advantageously employed, for example, benzhydrylamine resin, p-methylbenzhydrylamine resin, p-hydroxybenzoic acid resin and so on.

The reaction of the cyclic peptide on such a solid phase reaction resin can be conducted in the same manner as the conventional solid phase reaction and the cyclic peptide of general formula (V) can be used in a proportion of, for example, about 1.0 to 3.0 equivalents relative to the solid phase reaction resin.

The desired cyclic peptide or elcatonin can be obtained by subjecting the protected peptide thus synthesized on the solid phase reaction resin to the conventional deprotection procedure, preferably deprotection with an acid, for example hydrogen fluoride.

The reaction product can be isolated and purified by the conventional isolation and purification procedures such as gel permeation chromatography, ion exchange chromatography, partition chromatography, high performance liquid chromatography, reversed phase high performance liquid chromatography, electrophoresis and so on.

The cyclic peptide or elcatonin produced in accordance with the present invention is available as the free peptide or a salt thereof, depending on the conditions of the reaction. The free peptide and the salt can be interconverted by the conventional procedure. Pharmaceutically acceptable salts of the free peptide can be prepared by reacting it with inorganic acids such as hydrochloric acid, sulfuric acid, hydrobromic acid, phosphoric acid, etc. or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benzenesulfonic acid, toluenesulfonic acid and so on. The peptide and synthetic elcatonin may form complexes with inorganic or organic substances. As such substances, there may be mentioned inorganic compounds derived from metals such as calcium, magnesium, aluminum, cobalt, zinc, etc., particularly sparingly soluble salts such as the phosphates, pyrophosphates and polyphosphates of such metals, hydroxides of such metals, polyphosphates of alkali metals, and so on.

The cyclic peptide and synthetic elcatonin can be used in combination with organic substances for prolongation of their pharmacologic actions. Among such organic substances are non-antigenic gelatin, carboxymethylcellulose, sulfonate or phosphate ester of alginic acid, dextran, polyethylene glycol and other glycols, phytic acid, polyglutamic acid, protamine and so on.

The peptides of the invention and the cyclic peptides, particularly elcatonin, which can be provided by the method of the invention can be used for the treatment of hypercalcemia, osteoporosis and other diseases.

The following examples and reference examples are further illustrative but by no means limitative of the present invention.

EXAMPLES

The amino acid analysis in the examples and reference examples was invariably conducted by hydrolyzing the respective substances with 6N-hydrochloric acid at 110° C. for 24 hours and concentrating the hydrolyzate to dryness under reduced pressure.

Example 1

Production of (SEQ ID NO: 9)

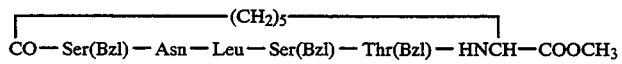

In 5 ml of TFA was dissolved 1.15 g of (SEQ ID NO: 10)

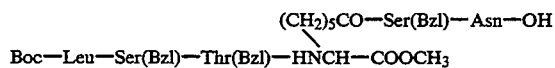

under ice-cooling and the solution was allowed to stand for 30 minutes. The reaction mixture was treated with ether and the resulting precipitate was recovered by filtration and dried in vacuo over potassium hydroxide to give 1.09 g of (SEQ ID NO: 10)

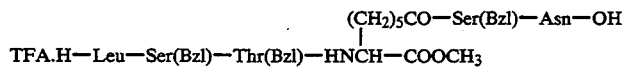

(yield 97.1%).
mp: 85°–88° C.
$[\alpha]_D^{24}$: +14.7° (c=1, DMF)
Rf: 0.17 (chloroform:methanol:water=40:10:1)

The resulting product was dissolved in 1 l of DMF and after the solution was neutralized with 0.12 ml of N-methylmorpholine under ice-cooling, 70.1 mg of NaCl, 89.5 mg of KCl, 50.9 mg of LiCl, 202 mg of CsCl, 0.45 g of WSC.HCl and 0.35 g of HOBt.H$_2$O were added. The mixture was stirred at room temperature for 96 hours and, then, concentrated under reduced pressure. To the residue was added 100 ml of H$_2$O. The oily product that separated out was washed with 50 ml of H$_2$O and after addition of 50 ml of 50% methanol, the mixture was incubated at 40° C. for 30 minutes. The resulting precipitate was filtered off and the filtrate was passed through an ion exchange resin column (0.8×5 cm). The eluate was concentrated to dryness under reduced pressure and the residue was dried in vacuo to give 0.72 g of a powder of the title compound (yield 70.3%).
mp: 201°–202° C.
$[\alpha]_D^{24}$: −24.7° (c=1, DMF)
Rf: 0.50 (chloroform:methanol=9:1)
Amino acid analysis: Asp 1.09(1), Thr 0.97(1), Ser 1.63(2), Leu 1.22(1), Aminosuberic acid 1.09(1)

Example 2

Production of (SEQ ID NO: 11)

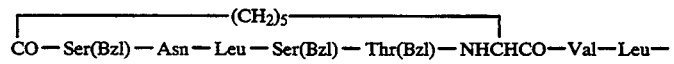

Gly—Lys(Cl—Z)—Leu—Ser(Bzl)—Gln—Glu(OBzl)—Leu—His(Tos)—

Lys(Cl—Z)—Leu—Gln—Thr(Bzl)—Tyr(Br—Z)—Pro—Arg(Tos)—

Thr(Bzl)—Asp(OBzl)—Val—Gly—Ala—Gly—Thr(Bzl)—Pro—NH-resin

To 20 ml of 30% TFA-methylene chloride was added 756 mg of (SEQ ID NO: 12) Boc-Lys-(Cl-Z)-Leu-Ser(Bzl)-Gln-Glu(OBzl)-Leu-His(Tos)-Lys(Cl-Z)-Leu-Gln-Thr(Bzl)-Tyr(Br-Z)-Pro-Arg(Tos)-Thr(Bzl)-Asp(OBzl)-Val-Gly-Ala-Gly-Thr (Bzl)-Pro-NH-resin and the mixture was stirred at room temperature for 30 minutes. Then, the resin was washed with 20 ml of methylene chloride for 1.5 minutes 6 times, 20 ml of 7% N-methylmorpholine-methylene chloride for 1.5 minutes twice, and 20 ml of methylene chloride for 1.5 minutes 6 times to give (SEQ ID NO: 12) H-Lys(Cl-Z)-Leu-Ser(Bzl)-Gln-Glu(OBzl)-Leu-His(Tos)-Lys(Cl-Z)-Leu-Gln-Thr(Bzl)-Tyr(Br-Z)-Pro-Arg(Tos)-Thr (Bzl)-Asp (OBzl)-Val-Gly-Ala-Gly-Thr(Bzl)-Pro-NH-resin.

The above resin was added to 20 ml of NMP followed by addition of 215 mg of (SEQ ID NO: 13)

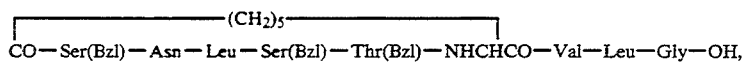
CO—Ser(Bzl)—Asn—Leu—Ser(Bzl)—Thr(Bzl)—NHCHCO—Val—Leu—Gly—OH, 64.5 mg of HOBt.H₂O and 86.8 mg of DCC, and the mixture was stirred at room temperature for 48 hours. After-completion of the reaction, the resin was washed with NMP, DMF, methanol and methylene chloride in that order and dried under reduced pressure to give 834 mg of the title compound (SEQ ID NO: 11)

reduced pressure and the residue was washed with ethyl ether and extracted with 50 ml of 1N aqueous acetic acid. The extract was lyophilized to give 352 mg of crude elcatonin.

The resulting crude elcatonin 352 mg was applied to a cation exchange column and linear gradient elution was carried out with ammonium acetate buffer. The eluate was monitored by high performance liquid chromatography and the fractions rich in the desired product elcatonin were pooled and lyophilized to give 100 mg of semi-purified elcatonin.

This semi-purified elcatonin, 100 mg, was purified by high performance liquid chromatography (column: Toso Corporation, TSK GEL ODS 120T, 2.15×30 cm, eluent: 0.1% TFA/CH₃CN=63/37, flow rate 8 ml/min.) to give 70 mg of elcatonin TFA salt.

This elcatonin TFA salt was applied to a cation exchange resin column and pH gradient elution with aqueous ammonium acetate was carried out. The fractions absorbing at 280 nm were pooled and lyophilized to recover 64 mg of a powder of elcatonin acetate.

mp: 240° C. (decomposition)

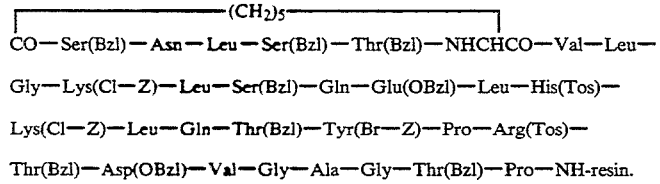
CO—Ser(Bzl)—Asn—Leu—Ser(Bzl)—Thr(Bzl)—NHCHCO—Val—Leu—

Gly—Lys(Cl—Z)—Leu—Ser(Bzl)—Gln—Glu(OBzl)—Leu—His(Tos)—

Lys(Cl—Z)—Leu—Gln—Thr(Bzl)—Tyr(Br—Z)—Pro—Arg(Tos)—

Thr(Bzl)—Asp(OBzl)—Val—Gly—Ala—Gly—Thr(Bzl)—Pro—NH-resin.

Example 3
Production of (SEQ ID NO: 1)

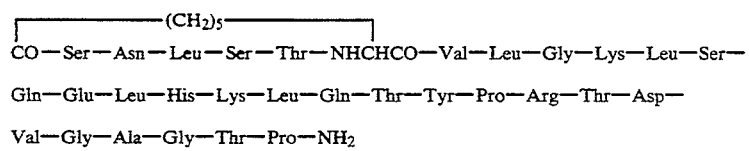
CO—Ser—Asn—Leu—Ser—Thr—NHCHCO—Val—Leu—Gly—Lys—Leu—Ser—

Gln—Glu—Leu—His—Lys—Leu—Gln—Thr—Tyr—Pro—Arg—Thr—Asp—

Val—Gly—Ala—Gly—Thr—Pro—NH₂

To 834 mg of (SEQ ID NO: 11)

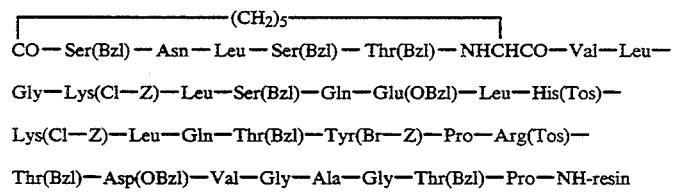
CO—Ser(Bzl)—Asn—Leu—Ser(Bzl)—Thr(Bzl)—NHCHCO—Val—Leu—

Gly—Lys(Cl—Z)—Leu—Ser(Bzl)—Gln—Glu(OBzl)—Leu—His(Tos)—

Lys(Cl—Z)—Leu—Gln—Thr(Bzl)—Tyr(Br—Z)—Pro—Arg(Tos)—

Thr(Bzl)—Asp(OBzl)—Val—Gly—Ala—Gly—Thr(Bzl)—Pro—NH-resin were added 0.9 ml of anisole and 9.0 ml of hydrogen fluoride and the mixture was stirred at 0° C. for 1 hour. The excess hydrogen fluoride was distilled off under $[\alpha]_D^{20}$: −93.1° (c=0.25, 0.1M aqueous acetic acid)
Rf: 0.39 (upper layer of water:n-butanol:acetic acid=5:4:1)

Amino acid analysis: Asp 2.07(2), Thr 3.69(4), Ser 2.59(3), Glu 3.03(3), Gly 3.13(3), Ala 1.10(1), Val 2.06(2), Leu 5.29(5), Tyr 1.03(1), Lys 2.08(2), His 0.84 (1), Arg 1.02 (1), Pro 2.03 (2), aminosuberic acid 1.05 (1)

Reference Example 1

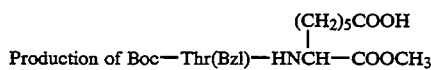

Production of Boc—Thr(Bzl)—HNCH—COOCH$_3$

In 40 ml of THF was dissolved 7.74 g of Boc-Thr(Bzl)-OH and after the solution was cooled to −15° C., 2.56 ml of N-methylmorpholine and 3.30 ml of isobutyl chloroformate were added dropwise in that order. The mixture was stirred at −15° C. for 1 minute to prepare the corresponding mixed anhydride. This reaction mixture was admixed with a DMF solution containing 5.08 g of L-aminosuberic acid-α-methyl ester and 3.50 ml of triethylamine and the mixture was stirred at 0° C. for 5 minutes and at room temperature for 1 hour and concentrated under reduced pressure. To the residue was added 400 ml of ethyl acetate and the mixture was washed successively with 100 ml of 10% citric acid twice, 100 ml of saturated aqueous sodium chloride solution twice, 100 ml of cold 5% aqueous sodium hydrogen carbonate solution 5 times and 100 ml of saturated aqueous sodium chloride solution twice. Each aqueous wash was extracted with 300 ml of ethyl acetate twice. Finally the ethyl acetate layer was dried over anhydrous sodium sulfate and concentrated under reduced pressure to give 11.56 g of the oily product.

Reference Example 2

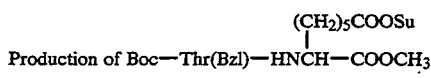

Production of Boc—Thr(Bzl)—HNCH—COOCH$_3$

In 40 ml of THF was dissolved 6.58 g of the oily product of

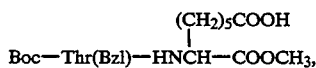

Boc—Thr(Bzl)—HNCH—COOCH$_3$, followed by addition of a THF solution containing 1.53 g of HOSu and 2.74 g of DCC under ice-cooling, and the mixture was stirred at 4° C. for 20 hours. The white substance dicyclohexylurea (DCU) was removed and the THF was then distilled off to give 7.87 g of the title compound as oil.

Reference Example 3

Production of Boc-Ser(Bzl)-Asn-OH

In 80 ml of H$_2$O was suspended 4.50 g of H-Asn-OH.H$_2$O, followed by addition of 80 ml of a THF solution containing 4.20 ml of triethylamine and 14.13 g of Boc-Ser(Bzl)-OSu under ice-cooling. The mixture was stirred at room temperature for 20 hours, after which the THF was distilled off. The residual aqueous solution was adjusted to pH 3 with 1M citric acid under ice-cooling and the resulting oily product was extracted with 200 ml of ethyl acetate. The extract was washed with 50 ml of saturated aqueous sodium chloride solution twice, dried over anhydrous sodium sulfate and concentrated under reduced pressure. The residue was treated with ether/petroleum ether (2:1) for solidification and the resultant powder was reprecipitated from methanol-isopropyl ether to give 8.74 g of Boc-Ser(Bzl)-Asn-OH (yield 71.2%).

mp: 138°–139° C.
[α]$_D^{22}$: 10.2° (c=1, DMF)
Rf: 0.54 (chloroform:methanol:acetic acid=7:2:1)
Amino acid analysis: Asp 1.14(1), Ser 0.86(1)

Reference Example 4 Production of (SEQ ID NO: 40)

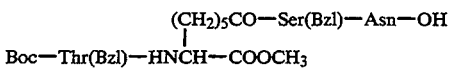

Boc—Thr(Bzl)—HNCH—COOCH$_3$

In 35 ml of TFA was dissolved 5.45 g of Boc-Ser(Bzl)-Asn-OH under ice-cooling and the solution was allowed to stand for 30 minutes. The reaction mixture was then treated with ether/petroleum ether (1:2) and the resulting precipitate was recovered by filtration and dried in vacuo over potassium hydroxide to give H-Ser-(Bzl)-Asn-OH.TFA.

This product was dissolved in 35 ml of DMF and the solution was neutralized with triethylamine under ice-cooling. To the mixture was added 35 ml of a DMF solution containing 7.87 g of

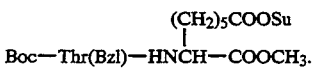

Boc—Thr(Bzl)—HNCH—COOCH$_3$.

The mixture was stirred at 0° C. for 1 hour and, then at 4° C. for 40 hours, after which the insoluble matter, present in a small quantity, was filtered off and the filtrate was concentrated under reduced pressure. To the residue was added 300 ml of ethyl acetate and the mixture was washed successively with 50 ml of cold 10% citric acid 3 times and 50 ml of H$_2$O twice and concentrated under reduced pressure. The residue was subjected to dilution with 30 ml of ethanol and subsequent distillation for a total of 3 times for dehydration and, then, treated with ether. The resulting precipitate was reprecipitated from methanol-ether to give 9.07 g of the title compound (yield 86.8%).

mp: 126°–128° C.
[α]$_D^{26}$: 4.6° (c=1, DMF)
Rf: 0.49 (chloroform:methanol:water=70:30:3)
Amino acid analysis: Asp 1.11(1), Thr 0.97(1), Ser 0.81(1), aminosuberic acid 1.11(1)

Reference Example 5 Production of (SEQ ID NO: 14)

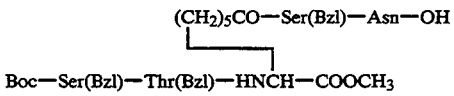

Boc—Ser(Bzl)—Thr(Bzl)—HNCH—COOCH$_3$

In 60 ml of TFA was dissolved 8.88 g of (SEQ ID NO: 40)

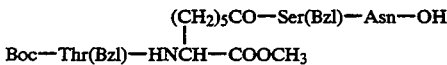

Boc—Thr(Bzl)—HNCH—COOCH$_3$ under ice-cooling and the solution was allowed to stand for 40 minutes, followed by treatment with ether/hexane (1:2). The resulting oily product was washed with hexane under cooling and dried in vacuo over potassium hydroxide.

This product was dissolved in 60 ml of DMF and neutralized with triethylamine under ice-cooling. Then, 40 ml of a solution containing 5.34 g of Boc-Ser(Bzl)-OSu in DMF was added. The mixture was stirred at 0° C. for 30 minutes and then at room temperature for 12 hours, at the end of which time it was concentrated under reduced pressure. The residue was diluted with 300 ml of ethyl acetate and washed successively with 50 ml of 10% citric acid twice and 50 ml of H₂O twice, followed by concentration under reduced pressure. The residue was diluted with 30 ml of ethanol and distilled. This procedure was repeated 3 times for dehydration. The residue was then solidified with isopropyl ether and reprecipitated from methanol-isopropyl ether to give 8.60 g of the title compound (yield 79.0%).

mp: 132°–133° C.
$[\alpha]_D^{25}$: 6.5° (c=1, DMF)
Rf: 0.56 (chloroform:methanol:water=70:30:3)
Amino acid analysis: Asp 1.17(1), Thr 1.01(1), Ser 1.70(2), aminosuberic acid 1.12(1)

Example 4 Production of (SEQ ID NO: 15)

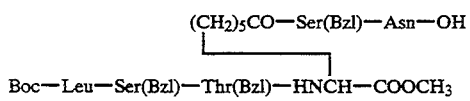

Boc—Leu—Ser(Bzl)—Thr(Bzl)—HNCH—COOCH₃

In 50 ml of TFA was dissolved 8.38 g of (SEQ ID NO: 14)

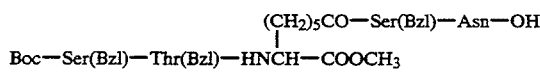

Boc—Ser(Bzl)—Thr(Bzl)—HNCH—COOCH₃ under ice-cooling and the solution was allowed to stand for 30 minutes. The reaction mixture was then treated with ether/petroleum ether (1:2) and the resulting oily product was washed with petroleum ether under cooling and dried in vacuo over potassium hydroxide.

The product was dissolved in 60 ml of DMF and after neutralization with triethylamine, 20 ml of a solution containing 3.00 g of Boc-Leu-OSu in DMF was added. The mixture was stirred at 0° C. for 30 minutes and at room temperature for 16 hours, and the reaction mixture was concentrated under reduced pressure. To the residue was added 300 ml of ethyl acetate and the mixture was washed successively with 50 ml of 10% citric acid twice and 50 ml of H₂O twice, followed by concentration under reduced pressure. The procedure of dilution with 30 ml ethanol and subsequent distillation was repeated 3 times for dehydration and the residue was solidified with ether and reprecipitated from methanol-isopropyl ether to give 7.92 g of the title compound (yield 84.6%).

mp: 150°–151° C.
$[\alpha]_D^{26}$: 3.3° (c=1, DMF)
Rf: 0.60 (chloroform:methanol:water=70:30:3)
Amino acid analysis: Asp 1.11(1), Thr 0.98(1), Ser 1.67(2), Leu 1.14(1), aminosuberic acid 0.91(1)

Reference Example 6

Production of (SEQ ID NO: 16)

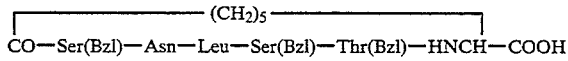

CO—Ser(Bzl)—Asn—Leu—Ser(Bzl)—Thr(Bzl)—HNCH—COOH

In 40 ml of DMF was dissolved 0.76 g of (SEQ ID NO: 9)

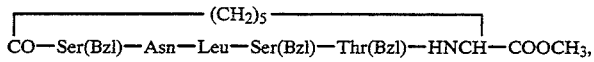

CO—Ser(Bzl)—Asn—Leu—Ser(Bzl)—Thr(Bzl)—HNCH—COOCH₃, followed by addition of 0.78 ml of 2N aqueous sodium hydroxide solution under ice-cooling. The mixture was stirred at 0° C. for 2 hours, after which 0.40 ml of 2N aqueous sodium hydroxide solution was further added. The mixture was stirred at 0° C. for 1 hour, neutralized with 2N-hydrochloric acid and concentrated under reduced pressure. The residue was diluted with 20 ml of H₂O and adjusted to pH 3 with 2N hydrochloric acid under ice-cooling and the resulting precipitate was recovered by filtration to give 0.70 g of the title compound (yield 94.6%).

mp: 166°–169° C.
$[\alpha]_D^{25}$: −19.4° (c=1, DMF)
Rf: 0.64 (chloroform:methanol:water=70:30:3)
Amino acid analysis: Asp 1.10(1), Thr 0.98(1), Ser 1.62(2), Leu 1.19(1), aminosuberic acid 1.10(1)

Reference Example 7

Production of Boc-Leu-Gly-OPac

In 30 ml of DMF was dissolved 9.87 g of TosOH.H-Gly-OPac and the solution was adjusted to pH 7 with N-methylmorpholine under cooling at −15° C.

On the other hand, 7.48 g of Boc-Leu-OH.H₂O and 4.59 g of HOBt.H₂O were dissolved in a mixture of 10 ml DMF and 30 ml THF and after the solution was cooled to 0° C., 20 ml of a THF solution containing 6.19 g of DCC was added and the mixture was stirred at 0° C. for 30 minutes. This solution was added to the solution prepared above and the mixture was stirred at −15° C. for 1 hour, at 0° C. for 2 hours and at 4° C. overnight. After completion of the reaction, the precipitate was recovered by filtration and concentrated under reduced pressure. The residue was dissolved in 200 ml of ethyl acetate, washed with 10% aqueous citric acid solution, 5% aqueous sodium hydrogen carbonate solution and saturated aqueous sodium chloride solution in that order, dried over anhydrous sodium sulfate and concentrated under reduced pressure. To the residue was added petroleum ether and the resulting precipitate was collected by filtration to give 8.93 g of the title compound Boc-Leu-Gly-OPac (yield 81.3%).

mp: 113°–113.5° C.
$[\alpha]_D^{20}$: −29.4° (c=1, methanol)
Rf: 0.66 (ethyl acetate:hexane=2:1)
Amino acid analysis: Gly 0.95(1), Leu 1.05(1)

Reference Example 8

Production of Boc-Val-Leu-Gly-OPac

Under ice-cooling, 4.00 g of Boc-Leu-Gly-OPac was dissolved by adding 50 ml of 4N HCl/dioxane and the solution was allowed to stand for 1 hour. The solution was then concentrated under reduced pressure to half its initial volume. To the residue was added ether-petroleum ether and the resulting precipitate was collected by filtration and dried under reduced pressure over potassium hydroxide. This dry product was dissolved in 40 ml of DMF and the solution was adjusted to pH 7 with N-methylmorpholine at −5° C. under ice-cooling. On the other hand, 2.57 g of Boc-Val-OH and 1.81 g of HOBt.H₂O were dissolved in 20 ml of DMF and 15 ml of a THF solution containing 2.44 g of DCC was added under ice-cooling. The mixture was stirred under ice-cooling for 30 minutes and at −5° C. for 20 minutes. This solution was mixed with the above-prepared solution and the mixture was stirred at −4° C. for 1 hour and at 4° C. for 3 days. After completion of the reaction, the reaction mixture was concentrated under reduced pressure and the residue was extracted with 150 ml of ethyl acetate. This ethyl acetate solution was washed with 1N aqueous citric acid solution, saturated aqueous sodium hydrogen carbonate solution and saturated aqueous sodium chloride solution in that order, dried over anhydrous magnesium sulfate and concentrated under reduced pressure. To the residue was added ethyl ether and the resulting precipitate was collected by filtration to give 4.12 g of the title compound Boc-Val-Leu-Gly-OPac (yield 84.4%).

mp: 148.5°–151° C.
$[\alpha]_D^{26}$: −21.5° (c=1, DMF)

Rf: 0.51 (chloroform:methanol:acetic acid=90:10:1)

Reference Example 9

Production of (SEQ ID NO: 17)

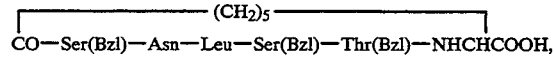

In 5 ml of TFA was dissolved 506 mg of Boc-Val-Leu-Gly-OPac under ice-cooling and the solution was allowed to stand for 30 minutes, followed by addition of petroleum ether. The resulting oily product was washed with petroleum ether a few times and dried under reduced pressure over potassium hydroxide. The dry product was dissolved in 20 ml of DMF and adjusted to pH 7 with N-methylmorpholine under ice-cooling.

To the above solution were added 462 mg of (SEQ ID NO: 16)

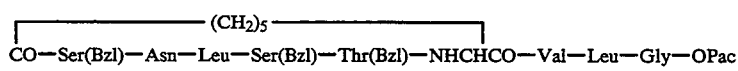

113 mg of HOBt.H₂O and 141 mg of WSC.HCl and the mixture was stirred at room temperature for 31 hours. After completion of the reaction, the reaction mixture was concentrated under reduced pressure and the residue was treated with 10% aqueous citric acid solution for solidification. This residue was washed with 1N aqueous citric acid solution, 5% aqueous sodium hydrogen carbonate solution and H₂O in that order and concentrated under reduced pressure. The resulting dry residue was further reprecipitated from methanol-ethyl acetate and the precipitate was recovered by filtration to give 296 mg of the title compound (SEQ ID NO: 17)

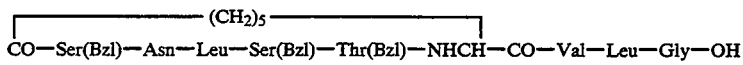

(yield 45.3%).
mp: 263° C. (decomposition)
$[\alpha]_D^{25}$: −17.9° (c=1, DMSO)
Rf: 0.57 (chloroform: methanol=6:1)
Amino acid analysis: Asp 1.04(1), Thr 0.93(1), Ser 1.51(2), Gly 1.10(1), Val 1.10(1), Leu 2.29(2), aminosuberic acid 1.04(1)

Reference Example 10

Production of (SEQ ID NO: 13)

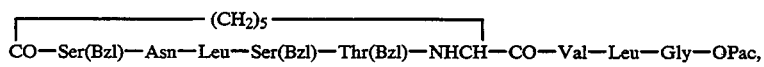

In 15 ml of DMF was dissolved 296 mg of (SEQ ID NO: 17)

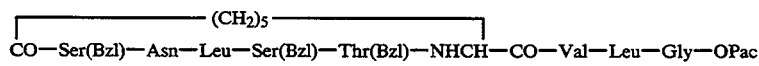

followed by addition of 7 ml of acetic acid and 1310 mg of powdery zinc. The mixture was stirred for 50 hours. After completion of the reaction, the mixture was filtered and the filtrate was concentrated. The residue was diluted with water and the precipitate was collected by filtration, further washed with water and dried under reduced pressure in the presence of phosphorus pentoxide. This dry product was further reprecipitated from methanol-ethyl ether and the precipitate was recovered by filtration to give 233 mg of the title compound (SEQ ID NO: 13)

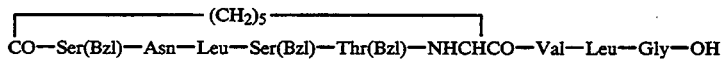

(yield 86.4%).
mp: 265° C. (decomposition)

$[\alpha]_D^{25}$: −17.9 (c=1, DMSO)
Rf: 0.46 (chloroform:methanol:water=70:30:3)
Amino acid analysis: Asp 1.05(1), Thr 0.93(1), Ser 1.53(2), Gly 1.12(1), Val 1.11(1), Leu 2.24(2), aminosuberic acid 1.02(1)

Reference Example 11

Production of (SEQ ID NO: 12)
Boc-Lys(Cl-Z)-Leu-Ser(Bzl)-Gln-Glu(OBzl)-Leu-His(-Tos)-Lys(Cl-Z)-Leu-Gln-Thr(Bzl)-Tyr(Br-Z)-Pro-Arg(Tos)-Thr(Bzl)-Asp(OBzl)-Val-Gly-Ala-Gly-Thr(Bzl)-Pro-NH Resin Using 1.19 g of p-methylbenzhydrylamine-polystyrene resin (0.42 mM NH$_2$/g resin, 1% divinylbenzene, 100-200 mesh, Institute of Peptide Research) as the atarting support, the following amino acid derivatives (all produced by Institute of Peptide Research) were sequentially subjected to condensation and de-Boc reaction by the technique of solid phase synthesis.

| | |
|---|---|
| Boc—Pro—OH | 430 mg |
| Boc—Thr(Bzl)—OH | 618 mg |
| Boc—Gly—OH | 350 mg |
| Boc—Ala—OH | 378 mg |
| Boc—Gly—OH | 350 mg |
| Boc—Val—OH | 434 mg |
| Boc—Asp(OBzl)—OH | 647 mg |
| Boc—Thr(Bzl)—OH | 618 mg |
| Boc—Arg(Tos)—OH | 1008 mg × 2 |
| Boc—Pro—OH | 430 mg |
| Boc—Tyr(Br—Z)—OH | 989 mg |
| Boc—Thr(Bzl)—OH | 618 mg |
| Boc—Gln—OH | 492 mg × 2 |
| Boc—Leu—OH | 500 mg |
| Boc—Lys(Cl—Z)—OH | 830 mg |
| Boc—His(Tos)—OH | 818 mg |
| Boc—Leu—OH | 500 mg |
| Boc—Glu(OBzl)—OH | 674 mg |
| Boc—Gln—OH | 492 mg × 2 |
| Boc—Ser(Bzl)—OH | 590 mg |
| Boc—Leu—OH | 500 mg |
| Boc—Lys(Cl—Z)—OH | 830 mg |

Among these amino acid derivatives, Boc-Arg(Tos)-OH and Boc-Gln-OH were first converted to the HOBt esters by the DCC-HOBt method and, then, respectively subjected to the condensation reaction. However, this condensation reaction was repeated twice. The other amino acid derivatives were first converted to the respective symmetric acid anhydrides by the DCC method prior to condensation.

In this manner, 2.18 g of (SEQ ID NO: 12) Boc-Lys(Cl-Z)-Leu-Ser(Bzl)-Gln-Glu(OBzl)-Leu-His(Tos)-Lys(Cl-Z)-Leu-Gln-Thr (Bzl)-Tyr(Br-Z)-Pro-Arg(Tos)-Thr(Bzl)-Asp(OBzl)-Val-Gly-Ala-Gly-Thr(Bzl)-Pro-NH-resin was obtained.

Example 5

Production of (SEQ ID NO: 18)

In 0.4 ml of TFA was dissolved 108 mg of (SEQ ID NO: 19)

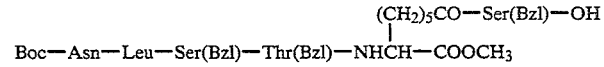

and the solution was allowed to stand at room temperature for 1 hour. The TFA was then distilled off under reduced pressure and the residue was treated with isopropyl ether. The resulting precipitate was recovered by filtration, washed with isopropyl ether and dried under reduced pressure over potassium hydroxide to give 102 mg of the title compound (97.1%).
mp: 170°-172° C.
$[\alpha]_D^{24}$: 3.7 (c=1, DMF)
Rf: 0.19 (chloroform:methanol:water=40:10:1)

Reference Example 12

Production of (SEQ ID NO: 19) 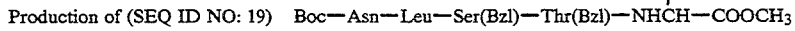

(1) Preparation of Boc-Ser(Bzl)-OPac

In 100 ml of ethyl acetate were dissolved 14.77 g of Boc-Ser(Bzl)-OH and 9.95 g of phenacyl bromide, followed by addition of 7 ml of triethylamine under ice-cooling. The mixture was stirred at 0° C. for 1 hour and then at room temperature for 4 hours. The reaction mixture was washed with saturated aqueous sodium hydrogen carbonate solution and saturated aqueous sodium chloride solution in that order, dried over anhydrous sodium sulfate and concentrated under reduced pressure. The residue was solidified with n-hexane and reprecipitated from ethyl acetate-n-hexane to give 18.1 g of the desired compound (yield 87.6%).
mp: 67°-68° C.
$[\alpha]_D^{24}$: −9.8° (c=1, methanol)
Rf: 0.87 (chloroform:methanol:water=90:10:1)

(2) Preparation of Boc-Leu-Ser(Bzl)-OPac

In 20 ml of TFA was dissolved 9,5 g of Boc-Ser(Bzl)-OPac under ice-cooling and the solution was allowed to stand at room temperature for 1 hour. The solution was ice-cooled again and 5.8 ml of 4N HCl/dioxane was added. The mixture was shaken well and n-hexane was added. The resulting precipitate was collected by filtration and dried under reduced pressure over potassium hydroxide. The dry product was dissolved in 20 ml of DMF and the solution was cooled to −10° C. or less and neutralized with 2.35 ml of N-methylmorpholine to pH 7.

On the other hand, 5.73 g of Boc-Leu-OH.H$_2$O and 3.87 g of HOBt.H$_2$O were dissolved in 10 ml of DMF and cooled to −10° C. or less. Then, 50 ml of a cold DMF solution containing 4.85 g of WSC.HCl was added and the mixture was stirred under ice-cooling for 30 minutes.

The above solution was cooled again to −10° C. or less and added to the above-prepared DMF solution and the mixture was stirred at −15° C. to −10° C. for 2 hours and, then, at 4° C. for 20 hours. After completion of the reaction, the reaction mixture was concentrated under reduced pressure and the residue was extracted with ethyl acetate. The extract was washed successively with 1N aqueous citric acid solution 5 times, saturated aqueous sodium chloride solution 5 times, saturated aqueous sodium hydrogen carbonate solution 10 times and saturated aqueous sodium chloride solution 5 times, then dried over anhydrous sodium sulfate and concentrated under reduced pressure. The residue was solidified with diethyl ether/petroleum ether (1:4) and reprecipitated from ethyl acetate-diethyl ether/petroleum ether (1:3) to give 9.71 g of the desired compound (yield 80.1%).

mp: 100°–101° C.
$[\alpha]_D^{24}$: −17.1° (c=1, methanol)
Rf: 0.66 (chloroform:methanol:water=90:10:1)

(3) Preparation of Boc-Leu-Ser(Bzl)-OH

In 100 ml of 90% aqueous acetic acid solution was dissolved 9.71 g of Boc-Leu-Ser(Bzl)-OPac, followed by addition of 36.1 g of powdery zinc under ice-cooling. The mixture was stirred at room temperature for 3 hours. After completion of the reaction, the reaction mixture was filtered and the filtrate was concentrated and extracted with ethyl acetate. The extract was washed successively with 1N aqueous citric acid solution 5 times and saturated aqueous sodium chloride solution 5 times, then dried over anhydrous sodium sulfate and concentrated under reduced pressure. The residue was solidified with petroleum ether and reprecipitated from ethyl acetate-petroleum ether to give 6.97 g of the desired compound (yield 92.7%).

mp: 73°–75° C.
$[\alpha]_D^{24}$: 3.0 (c=1, methanol)
Rf: 0.31 (chloroform:methanol:water=85:15:1)

(4) Preparation of 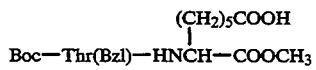

In 5 ml of 4N HCl/dioxane was dissolved 2.0 g of Boc-Ser(Bzl)-OPac under ice-cooling and the solution was allowed to stand at room temperature for 1 hour. The solution was then treated with n-hexane and the resulting precipitate was recovered by filtration and dried in vacuo over potassium hydroxide to give HCl.H-Ser(Bzl)-OPac. This product was dissolved in 5 ml of DMF and neutralized with N-methylmorpholine under cooling at −10° C. or less.

On the other hand, 2.61 g of $$\text{Boc—Thr(Bzl)—HNCH—COOCH}_3 \atop | \atop (\text{CH}_2)_5\text{COOH}$$

and 0.89 g of HOBt.H₂O were dissolved in 10 ml of DMF and the solution was cooled to −10° C. or less. Then, 30 ml of a cold DMF solution containing 1.11 g of WSC.HCl was added and the mixture was stirred under ice-cooling for 30 minutes.

This solution was cooled again to −10° C. or less and added to the DMF solution previously prepared above, and the mixture was stirred at −15° C. to −10° C. for 2 hours and then at 4° C. for 18 hours. After completion of the reaction, the reaction mixture was concentrated under reduced pressure and the residue was extracted with ethyl acetate/diethyl ether (1:1). The extract was washed successively with 1N aqueous citric acid solution 5 times, saturated aqueous sodium chloride solution 5 times, saturated aqueous sodium hydrogen carbonate solution 10 times and saturated aqueous sodium chloride solution 5 times, then dried over anhydrous sodium sulfate and concentrated under reduced pressure. The residue was treated with diethyl ether/petroleum ether (1:4) for solidification and reprecipitated from ethyl acetate-diethyl ether/petroleum ether (1:1) to give 2.44 g of the desired compound (yield 64.4%).

mp: 65°–67° C.
$[\alpha]_D^{24}$: −5.2° (c=1, methanol)
Rf: 0.64 (chloroform:methanol:water=90:10:1)

(5) Preparation of (SEQ ID NO: 20)

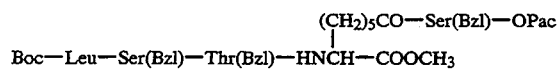

In 5 ml of TFA was dissolved 2.3 g of

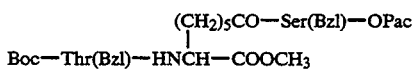

under ice-cooling and the solution was allowed to stand at room temperature for 1 hour. The solution was ice-cooled again and 2.2 ml of 4N HCl/dioxane was added. After shaking, diethyl ether/petroleum ether (1:1) was added and the resulting precipitate was recovered by filtration and dried under reduced pressure over potassium hydroxide. The dry product was dissolved in 10 ml of DMF, cooled to −10° C. or less and neutralized with N-methylmorpholine.

On the other hand, 1.61 g of Boc-Leu-Ser(Bzl)-OH and 0.66 g of HOBt.H₂O were dissolved in 10 ml of DMF and after the solution was cooled to −10° C. or less, 30 ml of a cold DMF solution containing 0.82 g of WSC.HCl was added. The mixture was stirred with ice-cooling for 30 minutes. This solution was chilled again to −10° C. or less and added to the DMF solution prepared above and the mixture was stirred at −15° C. to −10° C. for 2 hours and then at 4° C. for 56 hours. After completion of the reaction, the reaction mixture was concentrated under reduced pressure and the residue was extracted with ethyl acetate. The extract was washed successively with 1N aqueous citric acid solution 5 times, saturated aqueous sodium chloride solution 5 times, saturated aqueous sodium hydrogen carbonate solution 10 times and saturated aqueous sodium chloride solution 5 times, then dried over anhydrous sodium sulfate and concentrated under reduced pressure. The residue was treated with diethyl ether/petroleum ether (1:1) for solidification and reprecipitated from ethyl acetate-diethyl ether to give 1.47 g of the desired compound (yield 46.8%).

mp: 96°–98° C.
$[\alpha]_D^{24}$: −11.2° (c=1, methanol)
Rf: 0.68 (chloroform:methanol:water=90:10:1)

(6) Preparation of (SEQ ID NO: 21)

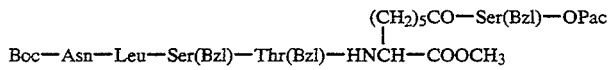

In 5 ml of TFA was dissolved 1.35 g of (SEQ ID NO: 20)

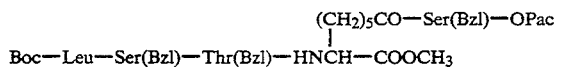

under ice-cooling and the solution was allowed to stand at room temperature for 1 hour. The solution was, then, ice-cooled again and 0.94 g of 4N HCl/dioxane was added. The mixture was shaken and treated with diethyl ether. The resulting precipitate was collected by filtration and dried under reduced pressure over potassium hydroxide. The dry product was dissolved in 10 ml of DMF and the solution was cooled to −10° C. or less and neutralized with N-methylmorpholine.

On the other hand, 0.44 g of Boc-Asn-OH and 0.32 g of HOBt.H₂O were dissolved in 10 ml of DMF and after the solution was cooled to −10° C. or less, 20 ml of a cold solution of 0.40 g of WSC.HCl in DMF was added. The mixture was stirred under ice-cooling for 30 minutes. This solution was cooled to −10° C. or less again and added to the DMF solution prepared above and the mixture was stirred at −10° C. to −5° C. for 30 minutes, under ice-cooling for 2 hours and at 4° C. for 21 hours. After completion of the reaction, the reaction mixture was concentrated under reduced pressure and the residue was treated with 1N aqueous citric acid under ice-cooling. The resulting precipitate was recovered by filtration, washed successively with 1N aqueous citric acid solution, H₂O, saturated aqueous sodium hydrogen carbonate solution and H₂O and dried under reduced pressure in the presence of phosphorus pentoxide. The dry product was suspended in methanol, followed by addition of ethyl acetate/diethyl ether (1:2) and the resulting precipitate was recovered by filtration to give 1.22 g of the desired compound (yield 81.9%).

mp: 177°–179° C.
[α]$_D^{24}$: −12.7° (c=1, DMF)
Rf: 0.54 (chloroform:methanol:water=85:15:1)
(7) Preparation of (SEQ ID NO: 19)

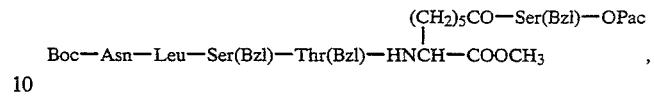

followed by addition of 1.04 g of powdery zinc under ice-cooling, and the mixture was stirred at room temperature for 3 hours. After completion of the reaction, the reaction mixture was filtered and the filtrate was concentrated. The residue was treated with H₂O and the resulting precipitate was collected by filtration and washed with H₂O, 50 mM ammonium bicarbonate buffer solution containing 25 mM EDTA (pH 8.0), H₂O, 1N aqueous citric acid solution and H₂O in this order and dried under reduced pressure in the presence of phosphorus pentoxide. The dry product was reprecipitated from DMF-diethyl ether to give 0.41 g of the desired compound (yield 71.9%).

mp: 174°–176° C.
[α]$_D^{24}$: −8.7° (c=1, DMF)
Rf: 0.35 (chloroform:methanol:water=40:10:1)
Amino acid analysis: Asp 1.13(1), Thr 0.95(1), Ser 1.52(2), Leu 1.21(1), aminosuberic acid 1.18(1)

Example 6

Production of (SEQ ID NO: 22)

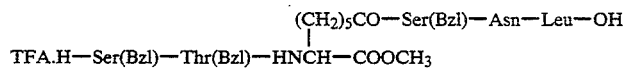

In 0.4 ml of TFA was dissolved 108 mg of (SEQ ID NO: 23)

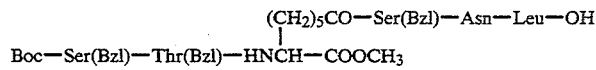

and the solution was allowed to stand at room temperature for 1 hour. The TFA was then distilled off under reduced pressure and the residue was treated with isopropyl ether. The resulting precipitate was collected by filtration, washed with isopropyl ether and dried under reduced pressure over potassium hydroxide to give 101 mg of the desired product (96.2%).

mp: 94°–97° C.
[α]$_D^{24}$: 3.3° (c=1, DMF)
Rf: 0.20 (chloroform:methanol:water=40:10:1)
Reference Example 13

Production of (SEQ ID NO: 23)

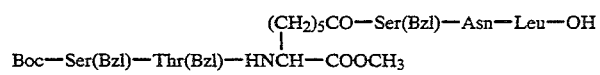

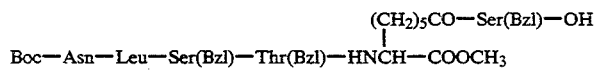

In 7 ml of 90% aqueous acetic acid solution was dissolved 0.63 g of (SEQ ID NO: 21)

(1) Preparation of Boc-Leu-OPac

In 100 ml of ethyl acetate were dissolved 4.99 g of Boc-Leu-OH.H₂O and 3.98 g of phenacyl bromide, followed by addition of 2.8 ml of triethylamine under ice-cooling. The mixture was stirred at under ice-cooling for 1 hour and then at room temperature for 4 hours. The reaction mixture was washed with saturated aqueous sodium hydrogen carbonate solution and saturated aqueous sodium chloride solution, dried over anhydrous sodium sulfate and concentrated under reduced pressure. The residue was solidified with n-hexane and the resulting precipitate was reprecipitated from ethyl acetate-n-hexane to give 6.6 g of the desired compound (yield 94.4%).

mp: 71°–72° C.
[α]$_D^{24}$: −47.5° (c=1, methanol)
Rf: 0.80 (chloroform:methanol:water=90:10:1)

(2) Preparation of Boc-Ser(Bzl)-Asn-Leu-OPac

In 5 ml of TFA was dissolved 2.0 g of Boc-Leu-OPac under ice-cooling and the solution was allowed to stand at room temperature for 1 hour. The solution was then ice-cooled again and 1.43 ml of 4N HCl/dioxane was added. After shaking, the mixture was treated with n-hexane and the resulting precipitate was collected by filtration and dried in vacuo over potassium hydroxide. The dry product was dissolved in 5 ml of DMF and the solution was cooled to −10° C. or less and neutralized with N-methylmorpholine.

On the other hand, 2.34 g of Boc-Ser(Bzl)-Asn-OH and 0.96 g of HOBt.H₂O were dissolved in 10 ml of DMF and after the solution was cooled to −10° C. or less, 30 ml of a cold DMF solution containing 1.21 g of WSC.HCl was added. The mixture was stirred under ice-cooling for 30 minutes. This solution was cooled to −10° C. or less again and added to the DMF solution prepared as above. The mixture was stirred at −10° C. to −5° C. for 30 minutes, under ice-cooling for 1 hour and at 4° C. for 16 hours. After completion of the reaction, the reaction mixture was concentrated under reduced pressure and the residue was solidified with 1N aqueous citric acid solution. The resulting precipitate was collected by filtration and washed with 1N aqueous citric acid solution, H₂O, saturated aqueous sodium hydrogen carbonate solution and H₂O in this order and dried under reduced pressure in the presence of phosphorus pentoxide. The dry product was reprecipitated from ethyl acetate-diethyl ether to give 2.33 g of the desired compound (yield 63.5%).

mp: 133°–135° C.
[α]$_D^{24}$: −9.6° (c=1, DMF)
Rf: 0.33 (chloroform:methanol:water=90:10:1)

(3) Preparation of (SEQ ID NO: 24)

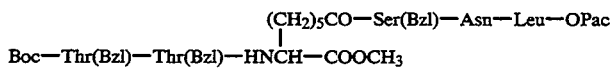

In 7 ml of TFA was dissolved 2.11 g of Boc-Ser(Bzl)-Asn-Leu-OPac under ice-cooling and the solution was allowed to stand at room temperature for 1 hour. The solution was then ice-cooled again and 2.5 ml of 4N HCl/dioxane was added. After shaking, the mixture was treated with diethyl ether and the resulting precipitate was collected by filtration and dried under reduced pressure over potassium hydroxide. The dry product was dissolved in 5 ml of DMF and the solution was cooled to −10° C. or less and neutralized with N-methylmorpholine.

On the other hand, 2.44 g of

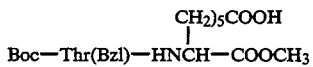

and 0.84 g of HOBt.H₂O were dissolved in 12 ml of DMF and after the solution was cooled to −10° C. or less, 20 ml of a cold DMF solution containing 1.04 g of WSC.HCl was added. The mixture was stirred under ice-cooling for 30 minutes. The solution was then cooled to −10° C. or less again and added to the DMF solution prepared as above and the mixure was stirred at −10° to −5° C. for 30 minutes, under ice-cooling for 2 hours and at 4° C. for 60 hours. After completion of the reaction, the reaction mixture was concentrated under reduced pressure and the residue was solidified with 1N aqueous citric acid solution. The resulting precipitate was collected by filtration and washed with 1N aqueous citric acid solution, H₂O, saturated aqueous sodium hydrogen carbonate solution and H₂O in the order mentioned and dried under reduced pressure over phosphorus pentoxide. The dry product was washed with methanol to give 2.45 g of the desired compound (yield 77.5%).

mp: 184°–186° C.
[α]$_D^{24}$: −8.4° (c=1, DMF)
Rf: 0.39 (chloroform:methanol:water=90:10:1)

(4) Preparation of (SEQ ID NO: 25)

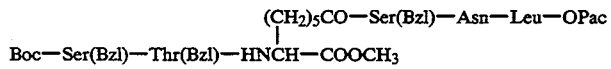

In 6 ml of TFA was dissolved 2.3 g of (SEQ ID NO: 24)

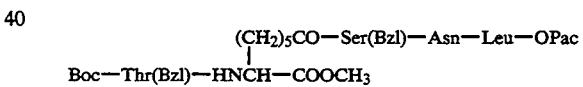

under ice-cooling and the solution was allowed to stand at room temperature for 1 hour. The solution was ice-cooled again and 1.7 ml of 4N HCl/dioxane was added. The mixture was shaken and, then, treated with diethyl ether. The precipitate was collected by filtration and dried under reduced pressure over potassium hydroxide. The resulting dry product was dissolved in 10 ml of DMF and the solution was cooled to −10° C. or less and neutralized with N-methylmorpholine.

On the other hand, 1.0 g of Boc-Ser(Bzl)-OH and 0.57 g of HOBt.H₂O were dissolved in 10 ml of DMF and after the solution was cooled to −10° C. or less, 20 ml of a cold DMF solution containing 0.71 g of WSC.HCl was added. The mixture was stirred under ice-cooling for 30 minutes. This solution was cooled to −10° C. or less again and added to the DMF solution prepared above and the mxiture was stirred at −15° C. to −10° C. for 2 hours and, then, at 4° C. for 20 hours. After completion of the reaction, the reaction mixture was concentrated under reduced pressure, the residue was solidified with 1N aqueous citric acid solution and the resulting precipitate was collected by filtration. The precipitate was washed with 1N aqueous citric acid solution, H₂O, saturated aqueous sodium hydrogen carbonate solution and H₂O in this order and dried under reduced pressure in the presence of phosphorus pentoxide. The dry product was suspended in methanol and treated with ethyl acetate/diethyl ether (1:2) and the resulting precipitate was collected by filtration to give 1.91 g of the desired compound (yield 70.7%).

mp: 178°–180° C.
[α]$_D^{24}$: −4.1° (c=1, DMF)
Rf: 0.51 (chloroform:methanol:water=85:15:1)

(5) Preparation of (SEQ ID NO: 23)

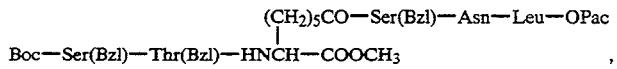

In 20 ml of 90% aqueous acetic acid solution was dissolved 1.58 g of (SEQ ID NO: 25)

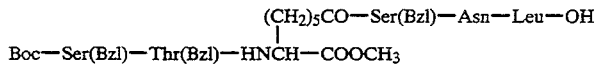

followed by addition of 2.59 g of powdery zinc under ice-cooling, and the mixture was stirred at room temperature for 3 hours. After completion of the reaction, the reaction mixture was filtered and the filtrate was concentrated and the residue was solidified by addition of H₂O. The resulting precipitate was collected by filtration and washed with H₂O, 50 mM ammonium bicarbonate buffer solution containing 25 mM EDTA (pH 8.0), H₂O, 1N aqueous citric acid solution and H₂O in the order mentioned and dried under reduced pressure in the presence of phosphorus pentoxide. The dry product was reprecipitated from DMF-diethyl ether to give 1.20 g of the desired compound (yield 84.5%).

mp: 159°–161° C.
[α]$_D^{24}$: 1.0° (c=1, DMF)
Rf: 0.30 (chloroform:methanol:water=40:10:1)
Amino acid analysis: Asp 1.16(1), Thr 0.93(1), Ser 1.52(2), Leu 1.21(1), aminosuberic acid 1.17(1)

Example 7

Production of (SEQ ID NO: 26)

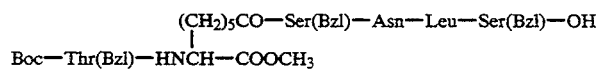

In 0.4 ml of TFA was dissolved 108 mg of (SEQ ID NO: 27)

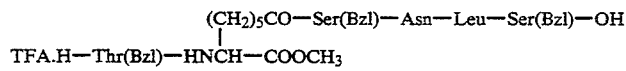

and the solution was allowed to stand at room temperature for 1 hour. The TFA was distilled off under reduced pressure and the residue was treated with isopropyl ether. The resulting precipitate was collected by filtration, washed with isopropyl ether and dried under reduced pressure over potassium hydroxide to give 104 mg of the desired compound (yield 99.0%).

mp: 157°–160° C.
[α]$_D^{24}$: 7.5° (c=1, DMF)
Rf: 0.30 (chloroform:methanol:water=40:10:1)

Reference Example 14

Production of (SEQ ID NO: 27)

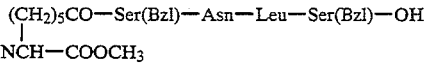

(1) Preparation of (SEQ ID NO: 28) Boc-Ser(Bzl)-Asn-Leu-Ser(Bzl)-OPac

In 5 ml of TFA was dissolved 1.8 g of Boc-Leu-Ser(Bzl)-OPac under ice-cooling and the solution was allowed to stand at room temperature for 1 hour. The solution was then ice-cooled again and 2.6 ml of 4N HCl/dioxane was added. After shaking, diethyl ether was added and the resulting precipitate was collected by filtration and dried under reduced pressure over potassium hydroxide. The dry product was dissolved in 5 ml of DMF and the solution was cooled to −10° C. or less and neutralized with N-methylmorpholine.

On the other hand, 1.47 g of Boc-Ser(Bzl)-Asn-OH and 0.60 g of HOBt.H₂O were dissolved in 10 ml of DMF and after the solution was cooled to −10° C. or less, 30 ml of a cold DMF solution containing 0.76 g of WSC.HCl was added. The mixture was stirred under ice-cooling for 30 minutes. This solution was cooled to −10° C. or less again and added to the DMF solution prepared as above. The mixture was stirred at −10° C. to −5° C. for 30 minutes, under ice-cooling for 1 hour and at 4° C. for 20 hours. After completion of the reaction, the reaction mixture was concentrated under reduced pressure and the residue was solidified by addition of 1N aqueous citric acid solution. The resulting precipitate was collected by filtration, washed with 1N aqueous citric acid solution, H₂O, saturated aqueous sodium hydrogen carbonate solution and H₂O in this order, and dried under reduced pressure in the presence of phosphorus pentoxide. The dry product was reprecipitated from methanol-diethyl ether to give 2.38 g of the desired compound (yield 85.3%).

mp: 156°-158° C.
[α]$_D^{24}$: −10.4° (c=1, DMF)
Rf: 0.34 (chloroform:methanol:water=90:10:1)

(2) Preparation of (SEQ ID NO: 29)

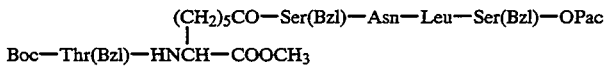
Boc—Thr(Bzl)—HNCH—COOCH$_3$

In 7 ml of TFA was dissolved 2.2 g of (SEQ ID NO: 28) Boc-Ser(Bzl)-Asn-Leu-Ser(Bzl)-OPac under ice-cooling and the solution was allowed to stand at room temperature for 1 hour. The solution was ice-cooled again and 2.0 ml of 4N HCl/dioxane was added. After shaking, the mixture was treated with diethyl ether and the resulting precipitate was collected by filtration and dried under reduced pressure over potassium hydroxide. The resulting dry product was dissolved in 10 ml of DMF and the solution was cooled to −10° C. or less and neutralized with N-methylmorpholine.

On the other hand, 2.0 g of

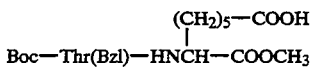
Boc—Thr(Bzl)—HNCH—COOCH$_3$ and 0.68 g of HOBt.H$_2$O were dissolved in 12 ml of DMF and after the solution was cooled to −10° C. or less, 20 ml of a cold DMF solution containing 0.85 g of WSC.HCl was added. The mixture was then stirred with ice-cooling for 30 minutes. This solution was cooled again and added to the DMF solution previously prepared as above and the mixture was stirred at −10° to 5° C. for 30 minutes, under ice-cooling for 1 hour and at 4° C. for 62 hours. After completion of the reaction, the reaction mixture was concentrated under reduced pressure and the residue was solidified with 1N aqueous citric acid solution. The resulting precipitate was collected by filtration, washed with 1N aqueous citric acid solution, H$_2$O, saturated aqueous sodium hydrogen carbonate solution and H$_2$O in this order and dried under reduced pressure in the presence of phosphorus pentoxide. The dry product was washed with methanol to give 2.5 g of the desired compound (yield 78.1%).
mp: 178°-180° C.

[α]$_D^{24}$: −6.5° (c=1, DMF)
Rf: 0.53 (chloroform:methanol:water=85:15:1)

(3) Preparation of (SEQ ID NO: 27)

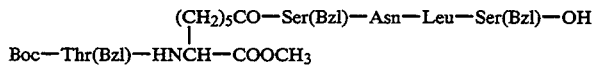
Boc—Thr(Bzl)—HNCH—COOCH$_3$

In 30 ml of 90% aqueous acetic acid solution was dissolved 2.4 g of (SEQ ID NO: 29)

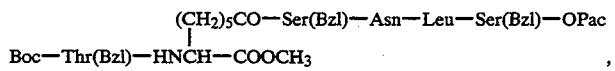
Boc—Thr(Bzl)—HNCH—COOCH$_3$ , followed by addition of 3.94 g of powdery zinc under ice-cooling, and the mixture was stirred at room temperature for 3 hours. After completion of the reaction, the reaction mixture was filtered and the filtrate was concentrated. The residue was solidified by addition of H$_2$O and the resulting precipitate was collected by filtration and washed with H$_2$O, 50 mM ammonium bicarbonate buffer solution containing 25 mM EDTA (pH 8.0), H$_2$O, 1N aqueous citric acid solution and H$_2$O in the order mentioned and dried under reduced pressure in the presence of phosphorus pentoxide. The dry product was reprecipitated from DMF-diethyl ether to give 1.95 g of the desired compound (yield 90.1%).
mp: 175°-177° C.
[α]$_D^{24}$: −1.6° (c=1, DMF)
Rf: 0.32 (chloroform:methanol:water=40:10:1)
Amino acid analysis: Asp 1.19(1), Thr 0.86(1), Ser 1.64(2), Leu 1.26(1), Aminosuberic acid 1.05(1)

Example 8

Production of (SEQ ID NO: 30)

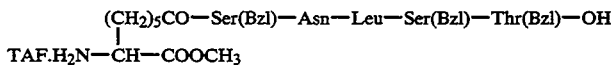
TAF.H$_2$N—CH—COOCH$_3$

In 0.4 ml of TFA was dissolved 108 mg of (SEQ ID NO: 31)

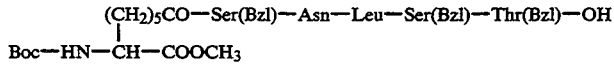
Boc—HN—CH—COOCH$_3$ and the solution was allowed to stand at room temperature for 1 hour. The TFA was then distilled off under reduced pressure and the residue was treated with isopropyl ether. The resulting precipitate was collected by filtration, washed with isopropyl ether and dried under reduced pressure over potassium hydroxide to give 102 mg of the desired compound (yield 97.1%).
mp: 165°-167° C.
[α]$_D^{24}$: 3.6° (c=1, DMF)
Rf: 0.28 (chloroform:methanol:water=40:10:1)

Reference Example 15

Production of (SEQ ID NO: 31)

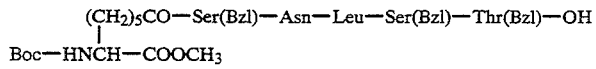

(1) Preparation of Boc-Thr(Bzl)-OPac

In 100 ml of ethyl acetate were dissolved 6.19 g of Boc-Thr(Bzl)-OH and 3.98 g of phenacyl bromide, followed by addition of 2.8 ml of triethylamine under ice-cooling, and the mixture was stirred for 1 hour and at room temperature for 4 hours. The reaction mixture was washed with saturated aqueous sodium hydrogen carbonate solution and saturated aqueous sodium chloride solution in that order, dried over anhydrous sodium sulfate and concentrated under reduced pressure to give 8.44 g of the desired compound (yield 98.7%).

(2) Preparation of Boc—HNCH—COOCH$_3$

In 50 ml of H$_2$O was dissolved 6.1 g of

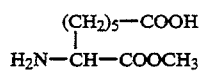

followed by addition of 4.2 ml of triethylamine and a solution of 7.2 g t-butyl dicarbonate in cold dioxane/H$_2$O (4:1) under ice-cooling. The mixture was stirred under ice-cooling for 15 minutes and, then, at room temperature for 30 minutes. After completion of the reaction, the dioxane was distilled off and the aqueous layer was adjusted to pH 10 with triethylamine under ice-cooling and washed with ethyl acetate. The aqueous layer was adjusted to pH 2 with 2M aqueous citric acid solution and extracted with ethyl acetate. The extract was washed with 1N aqueous citric acid solution and saturated aqueous sodium chloride solution in that order, dried over anhydrous sodium sulfate, and concentrated under reduced pressure. To the residue was added n-hexane and the resulting precipitate was collected by filtration and reprecipitated from ethyl acetate-n-hexane to give 8.03 g of the desired compound (yield 88.2%).

mp: 50°–51° C.

$[\alpha]_D^{24}$: −17.6° (c=1, methanol)

Rf: 0.38 (chloroform:methanol:water=90:10:1)

(3) Preparation of Boc-Leu-Ser(Bzl)-Thr(Bzl)-OPac

In 5 ml of 4N HCl/dioxane was dissolved 2.0 g of Boc-Thr(Bzl)-OPac under ice-cooling and the solution was allowed to stand at room temperature for 1 hour and, then, treated with n-hexane. The resulting precipitate was collected by filtration and dried under reduced pressure over potassium hydroxide. The resulting dry product was dissolved in 5 ml of DMF and the solution was cooled to −10° C. or less and neutralized with N-methylmorpholine.

On the other hand, 2.01 g of Boc-Leu-Ser(Bzl)-OH and 0.83 g of HOBt.H$_2$O were dissolved in 10 ml of DMF and after the solution was cooled to −10° C. or less, 30 ml of a cold DMF solution containing 1.04 g of WSC.HCl was added. The mixture was stirred under ice-cooling for 30 minutes. This solution was cooled to −10° C. or less again and added to the above DMF solution, and the mixture was stirred at −15° C. to −10° C. for 2 hours and, then, at 4° C. for 20 hours. After completion of the reaction, the reaction mixture was concentrated under reduced pressure and the residue was extracted with ethyl acetate. The extract was washed with 1N aqueous citric acid solution, saturated aqueous sodium chloride solution, saturated aqueous sodium hydrogen carbonate solution and saturated aqueous sodium chloride solution, then dried over anhydrous sodium sulfate and concentrated under reduced pressure. To the residue was added petroleum ether for solidification and the resulting precipitate was collected by filtration and reprecipitated from ethyl acetate-diethyl ether/petroleum ether (1:4) to give 2.54 g of the desired product (yield 75.6%).

mp: 53°–55° C.

$[\alpha]_D^{24}$: −14.2° (c=1, methanol)

Rf: 0.68 (chloroform:methanol:water=90:10:1)

(4) Preparation of (SEQ ID NO: 32) Boc-Ser(Bzl)-Asn-Leu-Ser(Bzl)-Thr(Bzl)-OPac

In 7 ml of TFA was dissolved 2.4 g of Boc-Leu-Ser(Bzl)-Thr(Bzl)-OPac under ice-cooling and the solution was allowed to stand at room temperature for 1 hour. The solution was ice-cooled again and 2.5 ml of 4N HCl/dioxane was added. After shaking, diethyl ether/petroleum ether (1:1) was added and the resulting precipitate was collected by filtration and dried under reduced pressure over potassium hydroxide. This dry product was dissolved in 10 ml of DMF and the solution was cooled to −10° C. or less and neutralized with N-methylmorpholine.

On the other hand, 2.12 g of Boc-Ser(Bzl)-Asn-OH and 0.87 g of HOBt.H$_2$O were dissolved in 20 ml of DMF and after the solution was cooled to −10° C. or less, 40 ml of a cold DMF solution containing 1.09 g of WSC.HCl was added. The mixture was stirred under ice-cooling for 30 minutes. This solution was cooled to −10° C. or less again and added to the above DMF solution. The mixture was stirred at −10° C. to −5° C. for 30 minutes, under ice-cooling for 2 hours and at 4° C. for 45 hours. After completion of the reaction, the reaction mixture was concentrated under reduced pressure and the residue was solidified by addition of 1N aqueous citric acid solution. The resulting precipitate was collected by filtration, washed with 1N aqueous citric acid solution, H$_2$O, saturated aqueous sodium hydrogen carbonate solution and H$_2$O in the order mentioned and dried under reduced pressure in the presence of phosphorus pentoxide. The dried product was reprecipitated from DMF-diethyl ether to give 2.83 g of the desired compound (yield 84.0%).

mp: 154°–156° C.

$[\alpha]_D^{24}$: −6.2° (c=1, DMF)

Rf: 0.36 (chloroform:methanol:water=90:10:1)

(5) Preparation of (SEQ ID NO: 33)

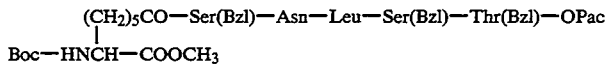

In 8 ml of TFA was dissolved 2.7 g of (SEQ ID NO: 32) Boc-Ser(Bzl)-Asn-Leu-Ser(Bzl)-Thr(Bzl)-OPac under ice-cooling and the solution was allowed to stand at room temperature for 1 hour. The solution was ice-cooled again and 2.0 ml of 4N HCl/dioxane was added. After shaking, diethyl ether was added and the resulting precipitate was collected by filtration and dried under reduced pressure over potassium hydroxide. This dried product was dissolved in 10 ml of DMF and solution was cooled to −10° C. or less and neutralized with N-methylmorpholine.

On the other hand, 1.8 g of

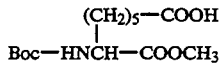

and 1.0 g of HOBt.H₂O were dissolved in 30 ml of DMF and after the solution was cooled to −10° C. or less, 40 ml of a cold DMF solution containing 1.24 g of WSC.HCl was added. The mixture was stirred under ice-cooling for 30 minutes. This solution was cooled to −10° C. or less again and added to the above DMF solution. The mixture was stirred at −10° C. to −5° C. for 30 minutes, under ice-cooling for 2 hours and at 4° C. for 65 hours. The reaction mixture was then concentrated under reduced pressure and the residue was solidified by addition of 1N aqueous citric acid solution. The resulting precipitate was collected by filtration, washed with 1N aqueous citric acid solution, H₂O, saturated aqueous sodium hydrogen carbonate solution and H₂O in the order mentioned, and dried under reduced pressure in the presence of phosphorus pentoxide. The dried product was suspended in methanol and ethyl acetate/-diethyl ether (1:2) was added. The resulting precipitate was collected by filtration to give 2.77 g of the desired product (yield 86.6%).

mp: 165°–167° C.
$[\alpha]_D^{24}$: −8.8° (c=1, DMF)
Rf: 0.50 (chloroform:methanol:water=85:15:1)

(6) Preparation of (SEQ ID NO: 31)

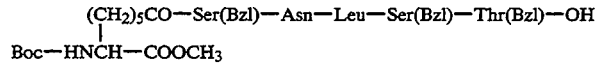

In 15 ml of 90% aqueous acetic acid solution was dissolved 1.44 g of (SEQ ID NO: 33)

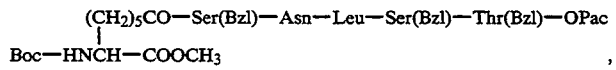

followed by addition of 2.37 g of powdery zinc under ice-cooling, and the mixture was stirred at room temperature for 3 hours. The reactions mixture was then filtered and the filtrate was concentrated. To the residue was added H₂O for solidification and the resulting precipitate was collected by filtration, washed with H₂O, 50 mM ammonium bicarbonate buffer solution containing 25 mM EDTA (pH 8.0), H₂O, 1N aqueous citric acid solution and H₂O in the order mentioned and dried under reduced pressure in the presence of phosphorus pentoxide. The dried product was reprecipited from DMF-diethyl ether to give 1.13 g of the desired compound (yield 86.8%).

mp: 183°–185° C.
$[\alpha]_D^{24}$: 2.5° (c=1, DMF)
Rf: 0.40 (chloroform:methanol:water=40:10:1)
Amino acid analysis: Asp 1.13(1), Thr 0.93(1), Ser 1.54(2), Leu 1.21(1), Aminosuberic acid 1.19(1)

Example 9

Production of (SEQ ID NO: 9)

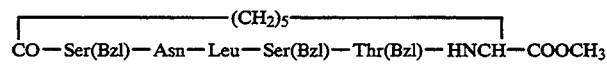

In 100 ml of DMF was dissolved 101 mg of (SEQ ID NO: 22)

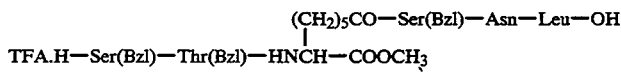

and the solution was neutralized with 10.2 μl of N-methylmorpholine under ice-cooling. Then, 16.8 mg of HOBt.H₂O and 21.1 mg of WSC.HCl were added and the mixture was stirred at room temperature for 24 hours to give 69 mg of the desired cyclization product (SEQ ID NO: 9)

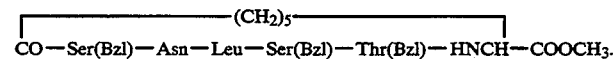

A cyclic peptide of (SEQ ID NO: 9)

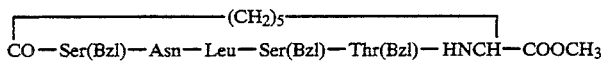

was prepared according to the following Examples 10 to 24.

Example 10

In 100 ml of DMF was dissolved 102 mg of (SEQ ID NO: 34)

and the solution was neutralized by addition of 10.2 μl of N-methylmorpholine under ice-cooling. To the solution were added 5.8 mg of NaCl, 7.5 mg of KCl, 4.2 mg of LiCl, 16.8 mg of CsCl, 16.8 mg of HOBt.H₂O and 21.1 mg of WSC.HCl and the mixture was stirred at room temperature for 24 hours to give 23.6 mg of the titled cyclic peptide (yield 24.6%). The amounts of all alkali metal salts relative to the peptide was 1.0 equivalent.

Example 11

The titled cyclic peptide 19.2 mg (yield 20.0%) was obtained in the same manner as in Example 10 except that 58.4 mg of NaCl, 74.6 mg of KCl, 42.4 mg of LiCl, 168.4 mg of CsCl, 16.8 mg of HOBt.H₂O and 21.1 mg of WSC.HCl were added to the solution. The amounts of all alkali metal salts to the peptide was 10 equivalents.

Example 12

In 100 ml of DMF was dissolved 102 mg of (SEQ ID NO: 18)

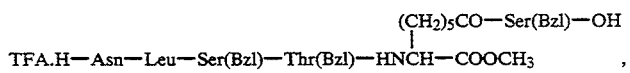

followed by addition of 10.2 μl of N-methylmorpholine under ice-cooling for neutralization. To the solution were added 16.8 mg of HOBt.H₂O and 21.1 mg of WSC.HCl and the mixture was stirred at room temperature for 24 hours to give 35.6 mg of the titled cyclic peptide (yield 37.2%).

Example 13

The titled cyclic peptide 35.6 mg (yield 37.2%) was obtained in the same manner as in Example 12 except that 5.8 mg of NaCl, 7.5 mg of KCl, 4.2 mg of LiCl, 16.8 mg of CsCl, 16.8 mg of HOBt.H₂O and 21.1 mg of WSC.HCl were added to the solution.

Example 14

The titled cyclic peptide 28.8 mg (yield 30.1%) was prepared in the same manner as in Example 12 except that 58.4 mg of NaCl, 74.6 mg of KCl, 42.4 mg of LiCl, 168.4 mg of CsCl, 16.8 mg of HOBt.H₂O and 21.1 mg of WSC.HCl were added to the solution.

Example 15

In 100 ml of DMF was dissolved 102 mg of (SEQ ID NO: 10)

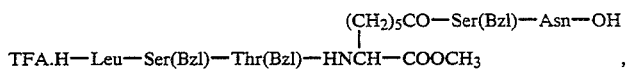

and the solution was neutralized by addition of 10.2 μl of N-methylmorpholine under ice-cooling. To the solution were added 16.8 mg of HOBt.H₂O and 21.1 mg of WSC.HCl and the mixture was stirred at room temperature for 24 hours to give 56.0 mg of the titled cyclic peptide (yield 58.5%).

Example 16

The titled cyclic peptide 60.8 mg (yield 63.5%) was prepared in the same manner as in Example 15 except that 58.4 mg of NaCl, 74.6 mg of KCl, 42.4 mg of LiCl, 168.4 mg of CsCl, 16.8 mg of HOBt.H₂O and 21.1 mg of WSC.HCl were added to the solution.

Example 17

In 100 ml of DMF was dissolved 101 mg of (SEQ ID NO: 22)

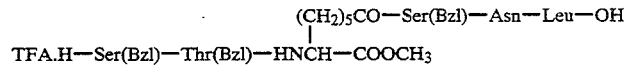

and the solution was neutralized by addition of 10.2 μl of N-methylmorpholine under ice-cooling. To the solution were added 5.8 mg of NaCl, 7.5 mg of KCl, 4.2 mg of LiCl, 16.8 mg of CsCl, 16.8 mg of HOBt.H₂O and 21.1 mg of WSC.HCl and the mixture was stirred at room temperature for 24 hours to give 64.4 mg of the titled cyclic peptide (yield 67.2%).

Example 18

The titled cyclic peptide 58.4 mg (yield 61.0%) was obtained in the same manner as in Example 17 except that 58.4 mg of NaCl, 74.6 mg of KCl, 42.4 mg of LiCl, 168.4 mg of CsCl, 16.8 mg of HOBt.H₂O, and 21.1 mg of WSC.HCl were added to the solution.

Example 19

In 100 ml of DMF was dissolved 104 mg of (SEQ ID NO: 26)

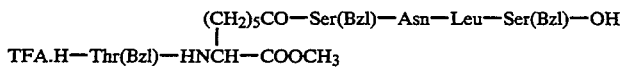

and the solution was neutralized with 10.2 μl of N-methylmorpholine. To the solution were added 16.8 mg of HOBt.H₂O and 21.1 mg of WSC.HCl and the mixture was stirred at room temperature for 24 hours to give 54.8 mg of the titled cyclic peptide (yield 57.2%).

Example 20

The titled cyclic peptide 51.2 mg (yield 53.4%) was obtained in the same manner as in Example 19 except that 5.8 mg of NaCl, 7.5 mg of KCl, 4.2 mg of LiCl, 16.8 mg of CsCl, 16.8 mg of HOBt.H₂O and 21.1 mg of WSC.HCl were added to the solution.

Example 21

The titled cyclic peptide 49.2 mg (yield 51.4%) was obtained in the same manner as in Example 19 except that 58.4 mg of NaCl, 74.6 mg of KCl, 42.4 mg of LiCl, 168.4 mg of CsCl, 16.8 mg of HOBt.H₂O and 21.1 mg of WSC.HCl were added to the solution.

Example 22

In 100 ml of DMF was dissolved 102 mg of (SEQ ID NO: 30)

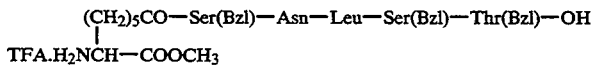

and the solution was neutralized by addition of 10.2 μl of N-methylmorpholine under ice-cooling. To the solution were added 16.8 mg of HOBt.H₂O, and 21.1 mg of WSC.HCl and the mixture was stirred at room temperature for 24 hours to give 62.0 mg of the titled cyclic peptide (yield 64.7%).

Example 23

The titled cyclic peptide 60.4 mg (yield 63.0%) was obtained in the same manner as in Example 22 except that 5.8 mg of NaCl2, 7.5 mg of KCl, 4.2 mg of LiCl, 16.8 mg of CsCl, 16.8 mg of HOBt.H₂O and 21.1 mg of WSC.HCl were added to the solution.

Example 24

The titled cyclic peptide 39.6 mg (yield 41.3%) was obtained in the same manner as in Example 22 except that 58.4 mg of NaCl, 74.6 mg of KCl, 42.4 mg of LiCl, 168.4 mg of CsCl, 16.8 mg of HOBt.H₂O and 21.1 mg of WSC.HCl were added to the solution.

Example 25

Production of (SEQ ID NO: 35)

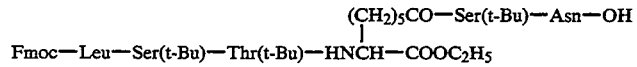

(1) The following peptide 9.98 g (yield 75.0%) (SEQ ID NO: 36)

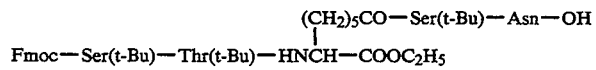

was prepared in the same manner as in Reference Examples 1 to 5 except that 9.94 g of Boc-Thr(t-Bu)-OH (wherein t-Bu represents tert-butyl group of a hydroxy-protective group) and 5.40 g of L-aminosuberic acid-α-ethyl ester were employed in replace with 7.74 g of Boc-Thr(Bzl)-OH and 5.08 g of L-aminosuberic acid-α-methyl ester in Reference Example 1, 17.3 g of Fmoc-Ser(t-Bu)-OSu (wherein Fmoc represents 9-fluorenyl-methyloxycarbonyl group of an amino-protective group) was employed in replace with 4.13 g of Boc-Ser(Bzl)-OSu in Reference Example 3, 6.53 g of Fmoc-Ser(t-Bu)-OSu was employed in replace with 5.43 g of Boc-Ser(Bzl)-OSu in Reference Example 5, and de-Fmoc reaction was conducted in 10% piperidine-DMF.

(2) The titled cyclic peptide 8.68 g (yield 78.2%) was obtained in the same manner as in Example 4 except that 9.79 g of the peptide prepared in the above step (1) was used.

Examples 26 to 30

In 100 ml of DMF was dissolved 101 mg of (SEQ ID NO: 22)

TABLE 1

| | compound(s) | amounts (mg) | temperature (°C.) | yield (mg) |
|---|---|---|---|---|
| Example 26 | DCC | 20.6 | 15 | 31.0 |
| Example 27 | WSC.HCl | 21.1 | 24 | 38.5 |
| Example 28 | HOBt.H₂O | 16.8 | −5 | 52.2 |
| | DCC | 20.6 | | |
| Example 29 | HOSu | 11.5 | 15 | 30.3 |
| | DCC | 20.6 | | |
| Example 30 | HOSu | 11.5 | 40 | 33.8 |
| | WSC.HCl | 21.1 | | |

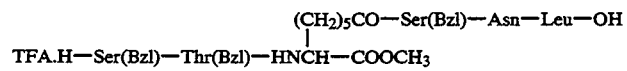

and the solution was neutralized by addition of 10.2 μl of N-methylmorpholine under ice-cooling. To the solution were added 5.8 mg of NaCl, 7.5 mg of KCl, 4.2 mg of LiCl, 16.8 mg of CsCl. The cyclic peptide of Example 17 was prepared in the same manner as in Example 17 except that compound(s) shown in Table 1 were used in replace with HOBt.H₂O and WSC.HCl in Example 17, and the mixture was stirred at a temperature shown in Table 1.

TABLE 1

|  | compound(s) | amounts (mg) | temperature (°C.) | yield (mg) |
|---|---|---|---|---|
| Example 26 | DCC | 20.6 | 15 | 31.0 |
| Example 27 | WSC.HCl | 21.1 | 24 | 38.5 |
| Example 28 | HOBt.H₂O | 16.8 | −5 | 52.2 |
|  | DCC | 20.6 |  |  |
| Example 29 | HOSu | 11.5 | 15 | 30.3 |
|  | DCC | 20.6 |  |  |
| Example 30 | HOSu | 11.5 | 40 | 33.8 |
|  | WSC.HCl | 21.1 |  |  |

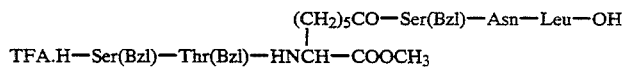

Examples 31 to 37

In 100 ml of DMF was dissolved 102 mg of (SEQ ID NO: 10)

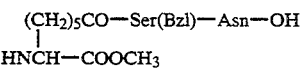

and followed by addition of 10.2 μl of N-methylmorpholine under ice-cooling for neutralization. To the solution were added alkali metal salt(s) shown in Table 2, 16.8 mg of HOBt.H₂O and 21.1 mg of WSC.HCl. The cyclic peptide of Example 15 was prepared according to the same manner as in Example 15 except that the mixture was stirred at a temperature shown in Table 2. The "equivalents" in Table 2 means equivalents of alkali metal salt(s) relative to the peptide to be cyclized.

TABLE 2

|  | alkali metal salts | amounts (mg) | equi-valents | temp-erature (°C.) | yield (mg) |
|---|---|---|---|---|---|
| Example 31 | NaCl | 58.4 | 10 | 40 | 42.0 |
| Example 32 | KCl | 746 | 100 | 0 | 18.3 |
| Example 33 | LiCl | 1696 | 400 | 20 | 13.0 |
| Example 34 | CsCl | 0.17 | 0.01 | 20 | 45.2 |
| Example 35 | NaCl | 0.58 | 0.1 | 20 | 47.2 |
|  | KCl | 7.46 | 1 |  |  |
| Example 36 | NaCl | 0.58 | 0.1 | −5 | 46.5 |

TABLE 2-continued

|  | alkali metal salts | amounts (mg) | equi-valents | temp-erature (°C.) | yield (mg) |
|---|---|---|---|---|---|
|  | LiCl | 4.24 | 1 |  |  |
| Example 37 | KCl | 0.75 | 0.1 | 20 | 42.8 |
|  | CsCl | 0.17 | 0.01 |  |  |

Examples 38 to 42

In 100 ml of DMF was dissolved 102 mg of (SEQ ID NO: 10)

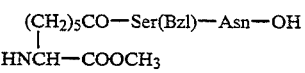

and followed by addition of 10.2 μl of N-methylmorpholine for neutralization. To the solution was added compound(s) shown in Table 3. The cyclic peptide of Example 15 was prepared in the same manner as in Example 15 except that the mixture was stirred at a temperature shown in Table 3.

TABLE 3

|  | compound(s) | amounts (mg) | temperature (°C.) | yield (mg) |
|---|---|---|---|---|
| Example 38 | DCC | 20.6 | 25 | 10.2 |
| Example 39 | WSC.HCl | 21.1 | 25 | 18.3 |
| Example 40 | HOBt.H₂O | 16.8 | 15 | 32.8 |
|  | DCC | 20.6 |  |  |
| Example 41 | HOSu | 11.5 | −5 | 25.1 |
|  | DCC | 20.6 |  |  |
| Example 42 | HOSu | 11.5 | 40 | 26.3 |
|  | WSC.HCl | 21.1 |  |  |

Examples 43 to 45

A cyclic peptide-resin of (SEQ ID NO: 11)

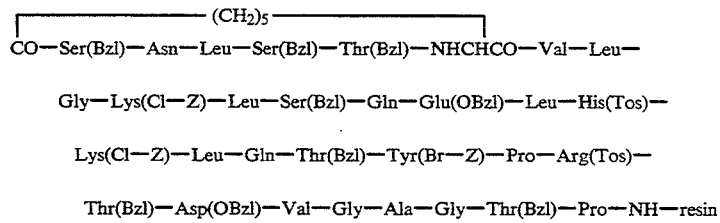

was prepared in the same manner as in Example 2 except that the following peptide-resin (SEQ ID NO: 12): H-Lys(Cl-Z)-Leu-Ser(Bzl)-Gln-Glu(OBzl)-Leu-His(Tos)-Lys(Cl-Z)-Leu-Gln-Thr(Bzl)-Tyr(Br-Z)-Pro-Arg(Tos)-Thr(Bzl)-Asp(OBzl)-Val-Gly-Ala-Gly-Thr(Bzl)-Pro-NH-resin and the following peptide (SEQ ID NO: 13):

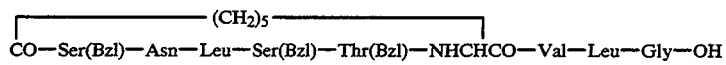

were used in proportions shown in Table 4, and the mixture was stirred at a temperature shown in Table 4. The "equivalents" in Table 4 means equivalents of the peptide relative to the peptide-resin.

TABLE 4

| | amounts of peptide (mg) | equi-valents | tempera-ture (°C.) | yield (mg) |
|---|---|---|---|---|
| Example 43 | 215 | 1.0 | 15 | 834 |
| Example 44 | 430 | 2.0 | 40 | 875 |
| Example 45 | 645 | 3.0 | −5 | 780 |

Example 46

A cyclic peptide-resin 792 mg of

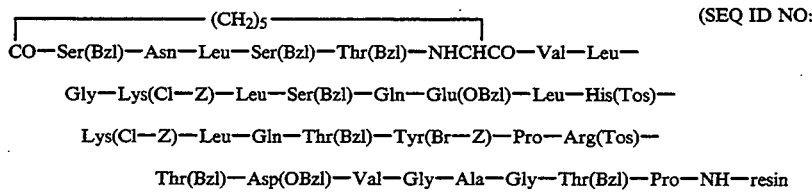

was prepared in the same manner as in Reference Example 11 and Example 2 except that 1.17 g of benzhydrylamine resin (0.42 mM NH₂/g resin, 1% divinylbenzene, 100 to 200 mesh: Institute of Peptide Research) was employed in replace with the solid phase reaction resin in Reference Example 11, and 64.5 mg of HOBt.H₂O and 807 mg of WSC.HCl were added in replace with HOBt.H₂O and WSC.HCl in Example 2.

Examples 47 and 48

The powdery elcatonin acetate of Example 3 was prepared in the same manner as in Example 3 except that 0.9 ml of anisole and hydrogen fluoride were added to 834 mg of the following cyclic peptide-resin (SEQ ID NO: 43)

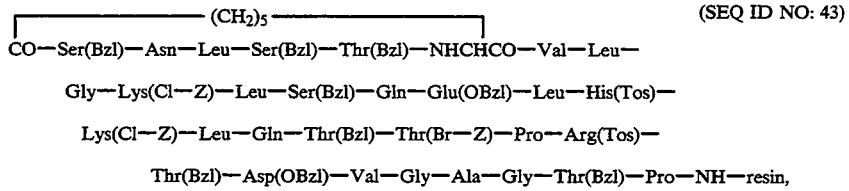

and the mixture was stirred at a temperature shown in Table 5 for 1 hour. Hydrogen fluoride 45 ml was added in Example 47, and hydrogen fluoride 90 ml was added in Example 48.

TABLE 5

| | temperature (°C.) | yield of elcatonin acetate (mg) |
|---|---|---|
| Example 47 | −5 | 62 |
| Example 48 | 10 | 58 |

What is claimed is:

1. A peptide of the following general formula (I)

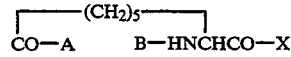 (I)

wherein A means Ser(X1)-Asn-Leu-Ser(X1)-Thr(X1)-OH (SEQ ID NO: 37), Ser(X1)-Asn-Leu-Ser(X1)-OH (SEQ ID NO: 38), Ser(X1)-Asn-Leu-OH, Ser(X1)-Asn-OH or Ser(X1)-OH; B means X2, X2-Thr(X1), X2-Ser(X1)-Thr(X1), X2-Leu-Ser(X1)-Thr(X1) or X2-Asn-Leu-Ser(X1)-Thr(X1)(SEQ ID NO: 39); X means a hydroxyl group, a carboxy-protecting group, an amino acid residue or a peptide residue and each amino acid residue may be protected with a protective group; X1 means a hydrogen atom or a hydroxy-protecting group; and X2 means a hydrogen atom or an amino-protecting group or an acid addition salt or complex compound thereof.

2. A peptide or an acid addition salt or complex compound thereof as claimed in claim 1, wherein A and B in general formula (I) are in any of the following combinations (1) through (5):

(1) A: Ser(X1)-Asn-Leu-Ser(X1)-Thr(X1)-OH (SEQ ID NO: 37)
B: X2

(2) A: Ser(X1)-Asn-Leu-Ser(X1)-OH (SEQ ID NO: 38)
B: X2-Thr(X1)

(3) A: Ser(X1)-Asn-Leu-OH
B: X2-Ser(X1)-Thr(X1)

(4) A: Ser(X1)-Asn-OH
B: X2-Leu-Ser(X1)-Thr(X1)

(5) A: Ser(X1)-OH
B: X2-Asn-Leu-Ser(X1)-Thr(X1)(SEQ ID NO: 39)

wherein X1 means a hydrogen atom or a hydroxy-protecting group; X2 means a hydrogen atom or an amino-protecting group.

3. A peptide or an acid addition salt or complex compound thereof as claimed in claim 1, wherein the carboxy-protecting group represented by X is an alkoxy group, a cycloalkyloxy group, an aralkyloxy group which may optionally be substituted, a substituted hydrazino group or a phenacyl group.

4. A peptide or an acid addition salt or complex compound thereof as claimed in claim 1, wherein the amino acid residue represented by X is Val-OH or Met-OH.

5. A peptide or an acid addition salt or complex compound thereof as claimed in claim 1, wherein the peptide residue represented by X is an oligopeptide residue of the following general formula (VII)

 (VII)

or a peptide residue of the following general formula (VIII)

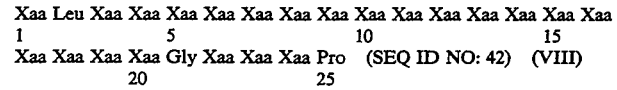

wherein:

Xaa at position 1 is Val or Met; Xaa at position 3 is Ser or Gly; Xaa at position 4 is Lys, Thr or Ala; Xaa at position 5 is Leu or Tyr; Xaa at position 6 is Ser, Thr or Trp; Xaa at position 7 is Gln, Lys or Arg; Xaa at position 8 is Glu, Asp or Asn; Xaa at position 9 is Leu or Phe; Xaa at position 10 is His or Asn; Xaa at position 11 is Lys or Asn; Xaa at position 12 is Leu, Phe or Thr; Xaa at position 13 is Gln or His; Xaa at position 14 is Thr or Arg; Xaa at position 15 is Tyr or Phe; Xaa at position 16 is Pro or Ser; Xaa at position 17 is Arg, Gly or Gln; Xaa at position 18 is Thr or Met; Xaa at position 19 is Asp, Ala, Asn or Gly; Xaa at position 20 is Val, Ile, Thr or Phe; Xaa at position 22 is Ala, Val, Pro or Ser; Xaa at position 23 is Gly or Glu; Xaa at position 24 is Thr or Ala; and Pro at position 25 is a prolinamide.

6. A peptide or an acid addition salt or complex compound thereof as claimed in claim 1, wherein the peptide residue represented by X is
-Val-Leu-Gly-OH or
-Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH₂ (SEQ ID NO: 5).

7. A peptide or an acid addition salt or complex compound thereof as claimed in claim 1, wherein the carboxy-protecting group on each amino acid residue is an alkoxy group, a cycloalkyloxy group, an aralkyloxy group which may optionally be substituted, a substituted hydrazino group or a phenacyl group.

8. A peptide or an acid addition salt or complex compound thereof as claimed in claim 1, wherein the amino-protecting group on each amino acid residue is an alkoxycarbonyl group which may optionally be substituted, a cycloalkyloxycarbonyl group which may optionally be substituted, an aralkyloxycarbonyl group which may optionally be substituted, an aralkyl group which may optionally be substituted or an acyl group which may optionally be substituted.

9. A process for producing a cyclic peptide of the following general formula (II) (SEQ ID NO: 3)

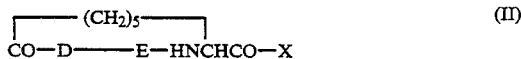
(II)

wherein D-E means Ser-Asn-Leu-Ser-Thr (SEQ ID NO: 44); X means a hydroxyl group, a carboxy-protecting group, an amino acid residue or a peptide residue; and each amino acid residue may be protected with a protective group, or an acid addition salt or complex compound thereof which comprises subjecting a peptide of the following general formula (III)

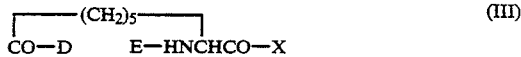
(III)

wherein D means Ser-OH, Ser-Asn-OH, Ser-Asn-Leu-OH, Ser-Asn-Leu-Ser-OH (SEQ ID NO: 45) or Ser-Asn-Leu-Ser-Thr-OH (SEQ ID NO: 44); E means H-Asn-Leu-Ser-Thr (SEQ ID NO: 46), H-Leu-Ser-Thr, H-Ser-Thr, H-Thr or a hydrogen atom; each amino acid residue may have been protected with a protective group; and X is as defined above to cyclization reaction.

10. A process for producing a cyclic peptide or an acid addition salt or complex compound thereof as claimed in claim 9, wherein said cyclization reaction is a chemical condensation reaction.

11. A process for producing a cyclic peptide or an acid addition salt or complex compound thereof as claimed in claim 9, wherein said cyclization reaction is conducted in the presence of an alkali metal halide.

12. A process for producing a cyclic peptide of the following general formula (II) (SEQ ID NO: 3)

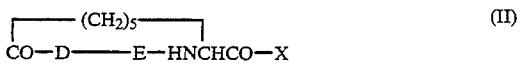
(II)

wherein D-E means Ser-Asn-Leu-Ser-Thr (SEQ ID NO: 44); X means a hydroxyl group, a carboxy-protecting group, an amino acid residue or a peptide residue; each amino acid residue may be protected with a protective group, or an acid addition salt or complex compound thereof which comprises subjecting a peptide of the following general formula (IV)

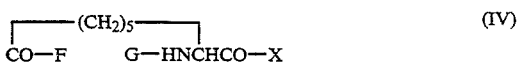
(IV)

wherein F means a hydroxyl group, an active ester residue, Ser-OH, Ser-Asn-OH, Ser-Asn-Leu-OH, Ser-Asn-Leu-Ser-OH (SEQ ID NO: 45) or Ser-Asn-Leu-Ser-Thr-OH (SEQ ID NO: 44); G means H-Ser-Asn-Leu-Ser-Thr (SEQ ID NO: 44), H-Asn-Leu-Ser-Thr (SEQ ID NO: 46), H-Leu-Ser-Thr, H-Ser-Thr, H-Thr or a hydrogen atom; each amino acid residue may have been protected with a protective group; and X is as defined above, to cyclization reaction in the presence of an alkali metal halide.

13. A process for producing a cyclic peptide or an acid addition salt or complex compound thereof as claimed in claim 12, wherein, provided that F in the peptide of general formula (IV) is a hydroxyl group or an active ester residue, said cyclization reaction is carried out by condensation between the activated side-chain carboxyl group of α-L-aminosuberic acid and the amino group of the N-terminal amino acid, with the hydroxyl groups of Ser and Thr having been protected.

14. A process for producing a cyclic peptide or an acid addition salt or complex compound thereof as claimed in claim 12, wherein said alkali metal halide is a halide of lithium, sodium, potassium, rubidium and cesium.

* * * * *